US008524891B2

(12) United States Patent
Hammer et al.

(10) Patent No.: US 8,524,891 B2
(45) Date of Patent: Sep. 3, 2013

(54) TETRAAZAPORPHYRIN-BASED COMPOUNDS AND THEIR USES

(75) Inventors: Robert P. Hammer, Baton Rouge, LA (US); Steven A. Soper, Baton Rouge, LA (US); Serhii Pakhomov, Baton Rouge, LA (US); Timothy J. Jensen, Mebane, NC (US); Michael W. Allen, Fitchburg, WI (US); Irina V. Nesterova, Baton Rouge, LA (US); Maria da Graça Henriques Vicente, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 1347 days.

(21) Appl. No.: 11/995,244

(22) PCT Filed: Jul. 14, 2006

(86) PCT No.: PCT/US2006/027561
§ 371 (c)(1),
(2), (4) Date: Sep. 22, 2008

(87) PCT Pub. No.: WO2007/009101
PCT Pub. Date: Jan. 18, 2007

(65) Prior Publication Data
US 2009/0215105 A1    Aug. 27, 2009

Related U.S. Application Data

(60) Provisional application No. 60/699,260, filed on Jul. 14, 2005.

(51) Int. Cl.
*C07D 487/22*    (2006.01)
*C07B 47/00*    (2006.01)

(52) U.S. Cl.
USPC .......................................... 540/145; 424/9.6

(58) Field of Classification Search
USPC .......................... 540/145; 422/430; 424/9.6
See application file for complete search history.

(56) References Cited

U.S. PATENT DOCUMENTS

| | | | | |
|---|---|---|---|---|
| 5,135,717 A | * | 8/1992 | Renzoni et al. | 422/430 |
| 5,346,670 A | | 9/1994 | Renzoni et al. | 422/52 |
| 5,494,793 A | | 2/1996 | Schindele et al. | 435/6 |

FOREIGN PATENT DOCUMENTS

| | | |
|---|---|---|
| EP | 0 502 723 | 9/1992 |
| WO | WO / 90/02747 | 3/1990 |
| WO | WO / 91/19007 | 12/1991 |

OTHER PUBLICATIONS

Karabörk, MuharremSerin, Selahattin Synthesis & Reactivity in Inorganic & Metal-Organic Chemistry; Oct. 2002, vol. 32 Issue 9, p. 1635, 13p.*

Aÿar, E. et al. in "Synthesis and Properties of 1,5-dithio-3-oxa-pentadiyl Bridged Polymeric Phthalocyanines," Dyes and Pigments 35: 269-278 (1997).
Aÿar, E. et al. in "Synthesis and spectroscopic investigations of IV-A group phthalocyanines containing macrocycle moieties". Dyes and Pigments. 36: 407-417 (1998).
Baumann, T. et al. in "solitaire-porphyrazines: Synthetic, structural, and spectroscopic investigation of complexes of the novel binucleating norphthalocyanine-2,3-dithiolato ligand". J. Am. Chem. Soc. 118: 10479-10486 (1996).
Bello, K. et al. in "Some observations on the visible absorption spectra and stability properties of the silicon phthalocyanine system". Dyes and Pigments 35: 261-267 (1997).
Brasseur, N. et al. in "Synthesis and Photodynamic Activities of Silicon 2,3-Naphthalocyanine Derivatives," J. Med. Chem. 34: 415-420 (1994).
Brasseur, N. et al. in "Photodynamic Activities and Skin Photosensitivity of the bis(dimethylthexylsiloxy) silicon 2,3-naphthalocyanine in Mice," Photochem. and Photobiol. 62: 1058-1065 (1995).
Brewis, M. et al. in "Silicon phthalocyanines with axial dendritic substituents". Angew. Chem. Int. Ed. 37: 1092-1094 (1998).
Cook, A. et al. in "Enantiomerically Pure "Winged" Spirane Porphyrazinoctaols," Angew. Chem. Int. Ed. Engl. 36:760-761 (1997).
Ding, X. et al. in "The Synthesis of Asymmetrically Substituted Amphiphilic Phthalocyanines and Their Gas-sensing Properties," Dyes and Pigments 40:187-191 (1999).
Flanagan, J. et al., 1997, reported that functionalized tricarbocyanine dyes could be used as near-infrared fluorescent probes for biomolecules. Bioconjugate Chem., 8(5): 751-756; J. Flanagan et al., 1998.
Ford, W. et al. in "Synthesis and Photochemical Properties of Aluminum, Gallium, Silicon, and Tin Naphthalocyanines," Inorg. Chem. 31: 3371-3377 (1992).
Forsyth, T. et al. in "A facile and regioselective synthesis of trans-heterofunctionalized porphyrazine derivatives". J. Org. Chem. 63: 331-336 (1998).
Griffiths, J. et al. in "Some observations on the synthesis of polysubstituted zinc phthalocyanine sensitizers for photodynamic therapy". Dyes and Pigments 33: 65-78 (1997).
Karabork, M. et al. in "Synthesis and characterization of phthalocyanines with non-ionic solubilizing groups". Synth. React. Inorganic Met.-Org. Chem. 1635-1647 (2002).
Kobayashi, N., "Optically active 'adjacent' type non-centrosymmetrically substituted phthalocyanines," Chem. Commun. pp. 487-488 (1998).

(Continued)

*Primary Examiner* — Paul V. Ward
(74) *Attorney, Agent, or Firm* — John H. Runnels

(57) ABSTRACT

Asymmetrically substituted metal-phthalocyanine compounds are disclosed. These compounds and other phthalocyanine-derivatives are used in bioimaging, bioanalysis, FRET and quenching techniques, photodynamic therapy, DNA analysis for cells, proteins, tissues and other biological entities, and other applications. Near-infrared fluorescence minimizes matrix effects typically seen in other methods of analyzing biochemical entities in cells, proteins, tissues and other biological entities.

18 Claims, 9 Drawing Sheets

(56) References Cited

OTHER PUBLICATIONS

Kobayashi, N. et al. in "Synthesis, spectroscopy, electrochemistry, and spectroelectrochemistry of a zinc phthalocyanine with D2h symmetry". Chem. Lett. pp. 2031-2034 (1992).

Kobayashi, N. et al. in "Phthalocyanines of a novel structure: Dinaphthotetraazaporphyrins with D2h symmetry", Inorg. Chem. 33: 1735-1740 (1994.

Leznoff, C. et al. in "Multisubstituted Phthalonitriles, Naphthalenedicarbonitriles, and Phenanthrenetetracarbonitriles as Precursors for Phthalocyanine Syntheses," Can. J. Chem. 73: 435-443 (1995).

Leznoff, C. et al. in "Synthesis and Photocytotoxicity of Some New Substituted Phthalocyanines," Photochem. and Photobiol. 49: 279-284 (1989).

Leznoff, C.al., 1994. "The Syntheses of 2,9,16,23-Tetrahydroxyphthalocyanines and 1,8,15,22-Tetrahydroxyphthalocyanines." Can. J. Chem. 72: 1990-1998.

Leznoff, C. et al., "The Synthesis of Phthalocyanines at Room Temperature." Chem. Commun. 1245-1246 (1996).

Mani, N. et al. in "Synthesis and characterization of porphyrazinoctamine derivatives: X-ray crystallographic studies of [2,3,7,8,12,13,17,18-octakis(dibenzylamino)-porphyrazinato] magnesium (II) and {2,3,7,8,12,13,17,18-octakis[allyl(benzyl)amino]-porphyrazinato} nickel (II)", J. Chem. Soc. Chem. Commun. pp. 2095-2096 (1994).

Montalban, A. et al. in "Seco-porphyrazines: Synthetic, structural, and spectroscopic investigations," J. Org. Chem. 62: 9284-9289 (1997).

Poupardin, O. et al. in "Rapid asymmetric synthesis of highly functionalized C5 chiral synthons. Practical preparation of trans-3-hydroxy-D-proline". Synlett. pp. 1279-1281.

Rosenthal, I. et al. in "The Effect of Substituents on Phthalocyanine Photocytotoxicity," Photochem. and Photobiol. 46: 959-963 (1987).

Sharman, W. et al. in "Novel water-soluble phthalocyanines substituted with phosphonate moieties on the benzo rings". Tetrahedron Letters 37: 5831-5834 (1996).

Sasmaz, S. et al. in "Synthesis and characterization of new phthalocyanines containing thio-oxa-ether moieties". Dyes and Pigments. 37: 223-230 (1998).

Terekhov, D. et al. in "Synthesis of 2,3,9,10,16,17,23,24-octaalkynylphthalocyanines and the Effects of Concentraion and Temperature on Their 1H NMR Spectra," J. Org. Chem. 61: 3034-3040 (1996).

Wu, Y. et al. In "Synthesis and Properties of Soluble Metal-free Phthalocyanines Containing Tetra- or Octa-alkyloxy Substituents," Dyes and Pigments 37: 317-325 (1998).

Ximing, D. et al. in "The synthesis and film-forming property of a new amphiphilic phthalocyanine". Dyes and Pigments 39: 223-229 (1998).

Yang. J. et al. in "Synthesis and characterization of a novel octaphenyl substituted solvent soluble phthalocyanine". J. Heterocyclic Chem. 32: 1521-1524 (1995).

Young, J. et al. in "Synthesis and characterization of di-disubstituted phthalocyanines". J. Org. Chem. 55: 2155-2159 (1990).

* cited by examiner

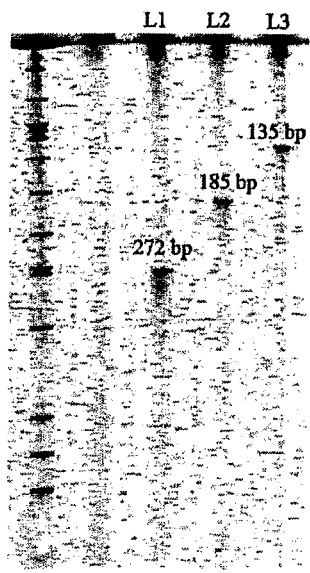 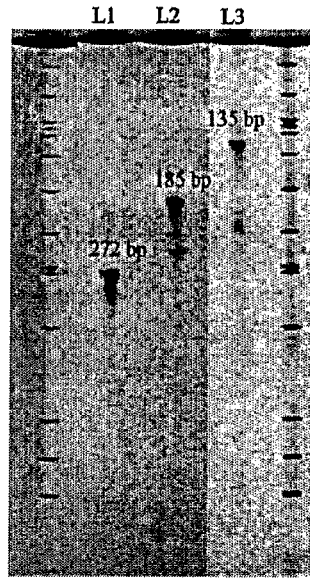 
Fig. 6A    Fig. 6B    Fig. 6C
 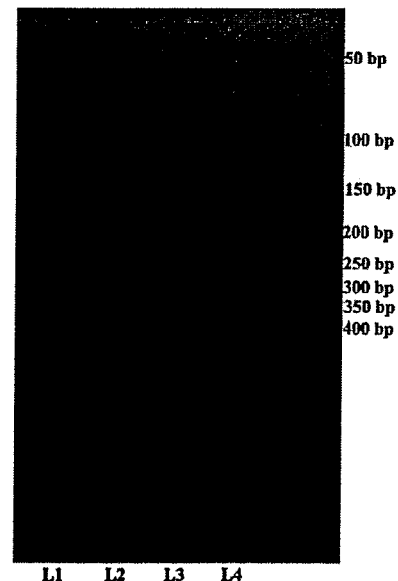
Fig. 6D    Fig. 6E

SEQUENCE LISTING

<160> NUMBER OF SEQ ID NOS: 7

<210> SEQ ID NO 1
<211> LENGTH: 17
<212> TYPE: DNA
<213> ORGANISM: Artificial sequence
<220> FEATURE:
<223> OTHER INFORMATION: Synthetic primer

<400> SEQUENCE: 1
gtaaaacgac ggccagt                                                  17

<210> SEQ ID NO 2
<211> LENGTH: 18
<212> TYPE: DNA
<213> ORGANISM: Artificial sequence
<220> FEATURE:
<223> OTHER INFORMATION: Synthetic primer

<400> SEQUENCE: 2
caactctctc agggccag                                                 18

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
ggccgattca ttaatgcagc                                               20

<210> SEQ ID NO 4
<211> LENGTH: 18
<212> TYPE: DNA
<213> ORGANISM: Artificial sequence
<220> FEATURE:
<223> OTHER INFORMATION: Synthetic primer

<400> SEQUENCE: 4
actctatagg cacccega                                                 18

<210> SEQ ID NO 5
<211> LENGTH: 17
<212> TYPE: DNA
<213> ORGANISM: Artificial sequence
<220> FEATURE:
<223> OTHER INFORMATION: Synthetic primer

<400> SEQUENCE: 5
gtgtggaatt gtgagcg                                                  17

<210> SEQ ID NO 6
<211> LENGTH: 24
<212> TYPE: DNA

```
<213> ORGANISM: Artificial sequence
<220> FEATURE:
<223> OTHER INFORMATION: Synthetic primer

<400> SEQUENCE: 6
gttggcatgc tttgatgacg cttc                                        24

<210> SEQ ID NO 7
<211> LENGTH: 25
<212> TYPE: DNA
<213> ORGANISM: Artificial sequence
<220> FEATURE:
<223> OTHER INFORMATION: Synthetic primer

<400> SEQUENCE: 7
gttttcctgg attatgcctg ggcac                                       25
```

TETRAAZAPORPHYRIN-BASED COMPOUNDS AND THEIR USES

This is the United States national stage of international application PCT/US2006/027561, filed 14 Jul. 2006, which claims the benefit of the Jul. 14, 2005 filing date of provisional patent application No. 60/699,260 under 35 U.S.C. §119(e).

The development of this invention was partially funded by the Government under grant R01 HG01499 awarded by the National Institutes of Health, and under grant number CHE-0304833, awarded by the National Science Foundation. The Government has certain rights in this invention.

TECHNICAL FIELD

This invention pertains to chemically robust near-infrared (near-IR) fluorophores, and new methods for their use, such as in bioimaging and sensitive bioanalytical applications, FRET and quenching techniques, photodynamic therapy ("PDT"), and specific targeting to proteins, cells, and tissues. Tetraazaporphyrins, including phthalocyanine ("Pc") macrocycles, are preferred compounds.

BACKGROUND ART

The development of labeling dyes that absorb and emit radiation in the near-IR (>600 nm) is important because at those wavelengths interferences from biological species are considerably reduced. The minimized "matrix" effects in the near-IR region result in part because Raman scattering cross-sections are low, and in part because there is reduced absorption and fluorescence from compounds that are typically present in complex biological matrices. In addition, the amount of light that penetrates through tissue typically doubles when the wavelength increases from 550 nm to 630 nm; this intensity doubles again when the wavelength increases from 630 nm to 700 nm, and intensity continues to systematically increase with longer wavelengths throughout the near-IR region. Also, the instrumentation used for detection of near-IR fluorescence is very sensitive with highly efficient single photon detectors, which use avalanche photodiodes and charge-coupled devises ("CCD"). With these sensitive fluorescence detectors one can in some instances detect species at the single-molecule level.

Fluorescence detection in the near-IR region has been demonstrated in a variety of bioanalytical applications: DNA sequencing (see Suzanne J. Lassiter, Wieslaw Stryjewski, Clyde V. Owens, James H. Flanagan, Jr., Robert P. Hammer, Shaheer Khan and Steven A. Soper, "Optimization of sequencing conditions using near-infrared lifetime identification methods in capillary gel electrophoresis," *Electrophoresis* 23, 1480-1489 (2002)); detecting DNA restriction fragments; ultra-sensitive analyses for micro-column separations; monitoring the presence of DNA in amplified polymeric chain reactions ("PCR") products; readout of DNA microarrays (see Yun Wang, Bikas Vaidya, Hannah D. Farquar, Wieslaw Stryjewski, Robert P. Hammer, Robin L. McCarley, Steven A. Soper, Yu-Wei Cheng and Francis Barany, "Microarrays assembled in microfluidic chips fabricated from poly(methyl methacrylate) for the detection of low-abundant DNA mutations," *Anal. Chem.* 75, 1130-1140 (2003)); DNA mutation detection (see Norman P. Gerry, Nancy E. Witowski, Joseph Day, Robert P. Hammer, George Barany, and Francis Barany, "Universal DNA Microarray Method for Multiplex Detection of Low Abundance Point Mutations," *J. Mol. Biol.*, 292, 251-262 (1999)); enzymatic substrate monitoring; and in FRET-based assays (see Musundi B. Wabuyele, Hannah Farquar, Wieslaw Stryjewski, Robert P. Hammer, Steven A. Soper Yu-Wei Cheng, and Francis Barany, "Approaching real-time molecular diagnostics: Single-pair fluorescence resonance energy transfer (spFRET) detection for the analysis of low abundant point mutations in K-ras oncogenes," *J. Am. Chem. Soc.* 125, 6937-6945 (2003)).

The major impediment to the use of near-IR fluorescence for various bioanalytical and bioimaging applications has been the lack of chemically robust fluorophores that also are water-soluble, and that exhibit low dark-toxicity. It is desirable that the photophysical properties, as well as the biological properties, of the fluorophores be tunable for particular uses by selectively altering the substituents, the central metal ion, or the axial ligands, while still retaining a very high photon yield. Also, the preferred fluorophore would be the one that would readily conjugate to target biological molecules, such as peptides, nucleic acids and proteins. Finally, when used as a biomarker, a fluorophore must show a high resistance to bleaching. There is an unfilled need for compounds having these properties.

Many commercially available dyes, such as cyanine dyes, are unstable to typical conjugation procedures and conditions, and therefore are not practical for conjugation to biomolecules. A typical commercial dye, such as a tricarbocyanine, exhibits a very low photon yield of approximately 10 photons/molecule.

Phthalocyanines have been used as commercial dyes for almost one hundred years. Pc-derivatives have a well-developed chemistry, and have been used in a wide variety of applications. However, there has been little focus on using phthalocyanines to label biological molecules or for cell staining.

There is an unfulfilled need for chemically robust phthalocyanines and related compounds that can be used in labeling, staining, bioanalytical procedures, including DNA sequencing, and that also can be functionalized to systematically conjugate with biological entities.

J. Flanagan et al., reported that functionalized tricarbocyanine dyes could be used as near-infrared fluorescent probes for biomolecules. *Bioconjugate Chem.*, 8(5): 751-756; J. Flanagan et al., 1998.

Near-infrared, heavy-atom-modified fluorescent dyes for base-calling in DNA-sequencing applications using temporal discrimination have been reported. *Anal. Chem.* 70 (13): 2676-2684.

U.S. Pat. Nos. 5,135,717 and 5,346,670, and Patent Cooperation Treaty Application WO 90/02747 disclose certain substituted phthalocyanines and related compounds, particularly aluminum phthalocyanines, and their use as dyes in DNA sequencing and other applications.

U.S. Pat. No. 5,494,793 discloses phthalocyanine derivatives monomerically conjugated with an antigen, antibody, oligonucleotide, or nucleic acid, and their use as detectable markers in DNA sequencing and other applications.

European Patent Application 0 502 723 A2 discloses certain tetrazaporphyrins said to be useful for labeling other molecules, and said to be useful in DNA sequencing and other applications.

Patent Cooperation Treaty Application WO 91/18007 discloses a detectably-labeled marker component that comprises a fluorophore moiety comprising a luminescent, substantially planar molecule structure coupled to two solubilizing polyoxyhydrocarbyl moieties, one located on either side of the planar molecular structure. Examples included certain substituted phthalocyanines and triazaporphyrins.

E. Ağar et al. "Synthesis and Properties of 1,5-dithio-3-oxa-pentadiyl Bridged Polymeric Phthalocyanines," *Dyes and Pigments* 35: 269-278 (1997) discloses certain oxa-thio bridged metal-free and metal phthalocyanine polymers.

Y. Wu et al. "Synthesis and Properties of Soluble Metal-free Phthalocyanines Containing Tetra- or Octa-alkyloxy Substituents," *Dyes and Pigments* 37: 317-325 (1998) discloses the synthesis of certain alkyloxy-substituted phthalocyanines.

X. Ding et al. "The Synthesis of Asymmetrically Substituted Amphiphilic Phthalocyanines and Their Gas-sensing Properties," *Dyes and Pigments* 40:187-191 (1999) discloses the synthesis of certain asymmetrically substituted amphiphilic phthalocyanines.

I. Rosenthal et al. "The Effect of Substituents on Phthalocyanine Photocytotoxicity," *Photochem. and Photobiol.* 46: 959-963 (1987) discloses the testing of several phthalocyanines for photobiological activity.

C. Leznoff et al. "Multisubstituted Phthalonitriles, Naphthalenedicarbonitriles, and Phenanthrenetetracarbonitriles as Precursors for Phthalocyanine Syntheses," *Can. J. Chem.* 73: 435-443 (1995) discloses the synthesis of several multisubstituted phthalonitriles, bisaromatic-o-dinitriles, naphthalenedicarbonitriles (5-substituted-2,3-dicyano naphthalenes), and phenanthrenetetracarbonitriles.

C. Leznoff et al. "Synthesis and Photocytotoxicity of Some New Substituted Phthalocyanines," *Photochem. and Photobiol.* 49:279-284 (1989) discloses certain ring-substituted phthalocyanines, and their testing for photodynamic activity.

W. Ford et al. "Synthesis and Photochemical Properties of Aluminum, Gallium, Silicon, and Tin Naphthalocyanines," *Inorg. Chem.* 31: 3371-3377 (1992) discloses the synthesis of several metal-containing naphthalocyanines said to be relevant in the search for photodynamic therapy agents.

N. Kobayashi, "Optically active 'adjacent' type non-centrosymmetrically substituted phthalocyanines," *Chem. Commun.* pp. 487-488 (1998) discloses the synthesis of optically active 'adjacent' type non-centrosymmetrically substituted phthalocyanines and benzo-substituted phthalocyanines.

N. Kobayashi, et al. "Aggregation, Complexation with Guest Molecules, and Mesomorphism of Amphiphilic Phthalocyanines Having Four- or Eight Tri(ethylene oxide) Chains," *Bull. Chem. Soc. Jpn,* 72: 1263-1271 (1999) discloses the synthesis of symmetrical phthalocyanines and zinc phthalocyanines.

N. Brasseur et al. "Synthesis and Photodynamic Activities of Silicon 2,3-Naphthalocyanine Derivatives," *J. Med. Chem.* 34: 415-420 (1994) discloses the synthesis of bis(tert-butyldimethylsiloxy)-, bis(dimethylthexylsiloxy)-, bis(tri-n-hexylsiloxy)-, and bis(dimethyloctadecylsiloxy)-silicon 2,3-naphthalocyanines, and their evaluation as potential photosensitizers for photodynamic therapy of cancer.

N. Brasseur et al. "Photodynamic Activities and Skin Photosensitivity of the bis(dimethylthexylsiloxy) silicon 2,3-naphthalocyanine in Mice," *Photochem. and Photobiol.* 62: 1058-1065 (1995), discloses complexes that have sensitivity in photodynamic therapy.

D. Terekhov et al. "Synthesis of 2,3,9,10,16,17,23,24-octaalkynylphthalocyanines and the Effects of Concentration and Temperature on Their $^1$H NMR Spectra," *J. Org. Chem.* 61: 3034-3040 (1996) discloses the synthesis of certain octaalkynylphthalocyanines, and discusses the effects that changes in concentration and temperature had on the NMR spectra of these compounds.

A. Cook et al. "Enantiomerically Pure "Winged" Spirane Porphyrazinoctaols," *Angew. Chem. Int. Ed. Engl.* 36:760-761 (1997) discloses the synthesis of certain enantiomerically pure porphyrazinoctaols.

A. Montalban et al. "Seco-porphyrazines: Synthetic, structural, and spectroscopic investigations," *J. Org. Chem.* 62: 9284-9289 (1997) discloses the synthesis of certain seco-porphyrazines (tetraazaporphyrins).

N. Kobayashi et al., "Phthalocyanines of a novel structure: Dinaphthotetraazaporphyrins with $D_{2h}$ symmetry", *Inorg. Chem.* 33:1735-1740 (1994) discloses the synthesis of certain isomerically pure naphthalene molecule-fused tetraazaporphyrins.

N. Mani et al. "Synthesis and characterization of porphyrazinoctamine derivatives: X-ray crystallographic studies of [2,3,7,8,12,13,17,18-octakis(dibenzylamino)-porphyrazinato]magnesium (II) and {2,3,7,8,12,13,17,18-octakis[allyl (benzyl)amino]-porphyrazinato}nickel (II)", *J. Chem. Soc. Chem. Commun.* pp. 2095-2096 (1994) discloses the synthesis of certain porphyrazinoctamine derivatives.

W. Sharman et al. "Novel water-soluble phthalocyanines substituted with phosphonate moieties on the benzo rings," *Tetrahedron Letters* 37: 5831-5834 (1996) discloses the synthesis of several phthalocyanine derivatives bearing phosphonate substituents directly bound to the aromatic rings of the phthalocyanine, and their possible use as photosensitizers in photodynamic therapy.

M. Brewis et al. "Silicon phthalocyanines with axial dendritic substituents," *Angew. Chem. Int. Ed.* 37:1092-1094 (1998) discloses certain silicon phthalocyanines substituted with various axial dendritic substituents.

J. Yang et al. "Synthesis and characterization of a novel octaphenyl substituted solvent soluble phthalocyanine," *J. Heterocyclic Chem.* 32: 1521-1524 (1995) discloses the synthesis of certain isomerically pure metal-free or zinc 1,2,3,4, 15,16,17,18-octaphenyl-9,10,23,24-tetradodecyloxyphthalocyanines.

J. Young et al. "Synthesis and characterization of di-disubstituted phthalocyanines," *J. Org. Chem.* 55: 2155-2159 (1990) discloses the synthesis of certain di-disubstituted phthalocyanines. This paper mentions that the regioselectivity of the usual manner of synthesizing phthalocyanines is poor, and gives mixtures of all possible orientation patterns for the substituents.

T. Baumann et al. "Solitaire-porphyrazines: Synthetic, structural, and spectroscopic investigation of complexes of the novel binucleating norphthalocyanine-2,3-dithiolato ligand," *J. Am. Chem. Soc.* 118: 10479-10486 (1996) discloses the synthesis of certain unsymmetrical metalloporphyrazines.

T. Forsyth et al. "A facile and regioselective synthesis of trans-heterofunctionalized porphyrazine derivatives," *J. Org. Chem.* 63: 331-336 (1998) discloses the synthesis of regiochemically defined porphyrazines, specifically certain phthalocyanines and derivatives.

E. Ağar et al. "Synthesis and spectroscopic investigations of IV-A group phthalocyanines containing macrocycle moieties," *Dyes and Pigments.* 36: 407-417 (1998) discloses the synthesis of certain substituted group IV-A (Si, Ge, Sn, and Pb) phthalocyanines.

J. Griffiths et al. "Some observations on the synthesis of polysubstituted zinc phthalocyanine sensitizers for photodynamic therapy," *Dyes and Pigments* 33: 65-78 (1997) discloses the syntheses and properties of certain polysubstituted zinc phthalocyanines, and their use as sensitizers for photodynamic therapy.

S. Şaşmaz et al. "Synthesis and characterization of new phthalocyanines containing thio-oxa-ether moieties," *Dyes and Pigments*. 37: 223-230 (1998) discloses the synthesis of certain metal-free and metal containing-phthalocyanines containing four 9-membered dithiaoxa macrocycles.

D. Ximing et al. "The synthesis and film-forming property of a new amphiphilic phthalocyanine," *Dyes and Pigments* 39: 223-229 (1998) discloses the synthesis of an amphiphilic, asymmetrical phthalocyanine.

K. Bello et al. "Some observations on the visible absorption spectra and stability properties of the silicon phthalocyanine system," *Dyes and Pigments* 35: 261-267 (1997) discloses the synthesis of a silicon phthalocyanine dye, and discusses its absorption spectra and stability.

N. Kobayashi et al. "Synthesis, spectroscopy, electrochemistry, and spectroelectrochemistry of a zinc phthalocyanine with $D_{2h}$ symmetry," *Chem. Lett.* 2031-2034 (1992) discloses a method for the synthesis of certain metallophthalocyanines.

M. Karabork et al. "Synthesis and characterization of phthalocyanines with non-ionic solubilizing groups," *Synth. React. Inorganic Met.-Org. Chem.* 1635-1647 (2002) discloses a method for the synthesis of some symmetrical ethylene glycol solubilized metal-free and metallated phthalocyanines.

Staining and Labeling

There is an unfilled need for improved methods for effective diagnostic applications, such as labeling or staining biological entities. Further, it is desirable that a family of compounds be available so that a single compound within the family of compounds can be tuned to have specific spectral properties. Such compounds could be used in developing methods for discrete discrimination of particular bases or mutations that may exist in biological samples. However, it is desirable that the differences between compounds within the family of compounds not substantially affect electrophoretic mobility. In addition, it is highly desirable that these compounds be readily conjugated with biological molecules of interest, e.g. to primers or to terminators, and that these compounds, and their conjugate complexes, be able to withstand the thermal and chemical conditions used in immunoassays and other biological assays. We are not aware of any reported compound family that meets these requirements. There is an unfilled need for the development of a suitable family of compounds that satisfies these criteria.

DNA Labeling and Sequencing

Of particular interest are improved methods for efficient DNA analysis. Reported methods use wavelength or color discrimination to differentiate probes or labels. However, it is difficult to use color discrimination to monitor more than 4 probes simultaneously in a single instrument. A major difficulty with color discrimination is the fact that absorption/emission bands tend to be broad, causing difficulties in efficient excitation across the dye set, cross-talk between detection channels due to inefficient filtering, or both—particularly where signal strength is low due to small sample size.

E. Waddell et al. reported "Time-resolved near-IR fluorescence detection in capillary electrophoresis," *J. Liq. Chrom. & Rel. Technol.*, vol. 23, pp. 1139-1158 (2000).U.S. Pat. No. 5,846,727 discloses a microsystem for rapid DNA sequencing.

Analysis of Mitochondria and Other Cellular Organelles

Of great interest are mitochondria and other cellular organelles. A reduction in the number of mitochondria can be an indication of certain diseases. Mitochondria have a diverse appearance, varying from round-shaped clusters to single-branched formations. Because the mitochondria have different shapes, mitochondrial staining agents are of interest to cell biologists. Methods for the selective identification of mitochondria is important for clinical research, microscopy and monitoring (both in vivo and in vitro analysis).

Several classes of mitochondria-selective stains have previously been reported. Fluorescent aromatic compounds are preferred since fluorescence detection limits are substantially lower than those of conventional light microscopic probes. The most widely used dye for mitochondria staining seems to be Rhodamine 123. The commonly used dyes are described below:

1. Fuchsine derivatives. These dyes are limited in use by the requirement that they be fixed with formalin or osmic acid in 1N HCl, or mercury dichloride, chromate or iron (II or III) salts.

2. Diaminobenzidine (DAB). This thermostable staining method is reversibly inhibited by 0.015M KCN.

3. Styryl dyes. These fluorescent probes have a large Stokes shift and can be used in concentrations $10^{-8}$ to $5 \times 10^{-6}$ M. However, the time required for uptake of this dye is long, and its quantum efficiency depends on characteristics of the solvent used.

4. Rhodamine and rosamine dyes. There are a number of dyes that are included within this family of dyes:

While the cytotoxicity of Rhodamine 123 was found to be low and the time required for uptake short, this reagent shows low photostability. Treatment with Dinitrophenol ("DNP") or with high concentrations of ethylene glycol bis(b-aminoethyl-ether)-N,N,N',N'-tetraacetic acid ("EGTA") and potassium chloride or sodium azide quench fluorescence. One limitation of this dye is that it is not usually retained in the cells when they are washed.

Fluorescent Mito Tracker Red (chloromethyl X-rosamine, Invitrogen), which is non-toxic in the dark at concentrations 100-250 nM, was found to be light toxic, inducing photosensitizing, depolarization of the mitochondrial membrane and causing apoptosis.

Mito Tracker Orange (chloromethyltetramethylrosamine), another widely used dye, causes mitochondrial depolarization. A chloromethyl group seems to be responsible for keeping the dye associated with the mitochondria via reaction with sulfhydryl reactive groups. The mitochondrial staining ability of both reagents is blocked by any membrane potential altering substance.

MitoTracker Green FM is essentially nonfluorescent in aqueous solutions, but becomes fluorescent when it is deposited in the hydrophobic, lipid environment of mitochondria. This dye accumulates in mitochondria regardless of mitochondrial membrane potential, and it is relatively photostable.

MitoFluor Green and Red Probes (Invitrogen), which also are relatively photostable, do not have chloromethyl moieties and thus are not retained in mitochondria.

5. Carbocyanines. Most carbocyanine dyes stain well when used at low concentrations (~0.5 µM or ~0.1 µg/mL), and they are known to be light-toxic. At higher concentrations or when used with cells having high mitochondrial membrane potentials, some representatives of this class (JC-1, Invitrogen) form fluorescent aggregates. The fluorescent emission maximum of these aggregates is shifted about 60 nm from the maximum observed from the non-aggregated species.

6. Nonyl acridine orange. This fluorescent dye stains mitochondria independently of the membrane potential and can be retained up to 10 days. The dye specifically binds to inner membranes, but it is toxic in high concentrations.

7. Avidins. Because biotinylated proteins (biotin carboxylase enzymes) are present almost exclusively in mitochondria, they can be somewhat selectively stained by fluorophore- or enzyme-labeled avidin or streptavidin derivatives. However, unless labeling is performed outside of the cell in vitro, high fluorescence backgrounds are typically observed.

Another example of a cellular organelle is the endoplasmic reticulum (ER), which is the biomolecular factory of the cell. It is here that proteins are made from the genetic information encoded in DNA. New lipids and membranes are also synthesized within the ER system. The ER also plays a role in detoxification of the cell. The ER membrane is chemically very similar to the outer membrane of mitochondria, so stains that label one membrane type will often, but not always, label both types simultaneously.

Stains that are commonly used to label the ER include:

The short chain carbocyanine dye dihexaoxacarbocyanine iodide ($DiOC_6$) labels both the ER and mitochondria. It is highly fluorescent. However, staining can lead to changes in the morphology of the organelles and toxic effects have been noted.

Rhodamine 6G and the hexyl ester of rhodamine B have similar staining characteristics as $DiOC_6$ but with less toxicity and a different fluorescence wavelength.

Long chain versions of $DiIC_{16}$ (3) (1,1'-dihexadecyl-3,3,3',3'-tetramethylindocarbocyanineperchlorate) and $DiIC_{18}$ (3) (1,1'-dioctadecyl-3,3,3',3'-tetramethylindocarbocyanine perchlorate have been used to label ER membranes. However, these probes require direct microinjection of the dyes into the cells. This is not a convenient or desirable method of delivery for the dye.

ER-Tracker Blue-White DPX (Invitrogen). Unlike $DiOC_6$, this dye selectively stains the ER and not the mitochondria, and has low toxicity.

ER-Tracker Green and ER-Tracker Red (Invitrogen). These dyes are drug conjugates of glibenclamide BODIPY FL and glibenclamide BODIPY TR, respectively. The glibenclamide moiety binds to sulphonylurea receptors of ATP sensitive potassium channels which are found on the ER. This may lead to variable staining of some cell types due to differential expression of these receptors.

Photodynamic Therapy

Compounds that show light toxicity can be useful as photosensitizers in photodynamic therapy ("PDT"). When cells or living tissues are treated with compounds that become active when exposed to light of a certain wavelength, the cells or tissues can be selectively destroyed.

While not wishing to be bound by this theory, it appears that when an appropriate compound is bound to mitochondria or endoplasmic reticulum in a cell, subsequent exposure of targeted tissue to actinic light produces reactive singlet oxygen in situ, leading to cell death via apoptosis. Unlike necrosis, apoptosis is an orderly process that does not provoke an immune system response. Killing unwanted tissue, e.g., tumor tissue, via apoptosis is preferred over necrosis, as it will generally produce fewer unwanted consequences for the patient. Photodynamic therapy has been used, for example, in treating macular degeneration in the eyes, in treating some skin and throat cancers, and in targeting bacterial and viral pathogens.

M. Hu et al. "Hydroxyphthalocyanines as potential photodynamic agents for cancer therapy," *J. Med. Chem.* 41:1789-1802 (1998) discloses several substituted zinc hydroxyphthalocyanines, and their use as possible photodynamic agents for use against cancer. However, it appears that the disclosed PDT agents destroy cells via necrosis, not apoptosis.

Fluorescence resonance energy transfer is a nonradiative process of energy transfer from an excited state fluorophore (donor) to a chromophore (acceptor). An important characteristic of the process is that the energy transfer rate varies inversely with the $6^{th}$ power of the donor-acceptor separation distance ($r^6$) over the range of 1-10 nm. Thus, by monitoring changes in FRET (e.g. its occurrence or distortion), it is possible to observe changes in the degree of proximity of the FRET fluorophores. FRET-based probes can be used in a variety of in vitro and in vivo DNA-analysis methods such as DNA hybridization detection, PCR monitoring, DNA mutation, cleavage, ligation, recombination detection, RNA synthesis monitoring, as DNA sequencing primers, and for DNA-based biosensors. There is a special interest in developing methods for analyzing complex biological samples using very sensitive FRET-based near-IR detection systems. Those systems would allow multiplexed analysis due to the FRET-capability combined with low interferences from background and availability of the cheap diode lasers for detection in the near-IR.

SUMMARY OF THE INVENTION

We have discovered novel asymmetric phthalocyanines and tetraazaporphrins, which may be used for purposes including staining, labeling, as PDT reagents, for bioanalytical studies, or for DNA analysis. We also have discovered that other phthalocyanines may also be used for similar purposes including staining, labeling, as PDT reagents, for bioanalytical studies, or for DNA analysis. In addition, we have synthesized several symmetric phthalocyanines, that to our knowledge have never been made before, that also may be used for similar purposes including staining, labeling, as PDT reagents, for bioanalytical studies, or for DNA analysis. These complexes exhibit very high photon emission yields in the near-IR region, improving sensitivity for detection. For example, one of our typical Pc dyes can produce a fluorescence yield of about $10^5$ photons/molecule, while the known dyes, such as tricarbocyanines, typically produce only approximately 10 photons/molecule. Improvement in the photon yields with chemically robust near-IR fluorophores, as reported here, could revolutionize both bioimaging and bioanalysis. Furthermore, some of these complexes also show an ability to conjugate with biological entities of interest, such as peptides, proteins and nucleic acids. Both FRET and quenching analyses have been done with these Pc-based compounds.

We have discovered novel metallo-Pc systems that are excellent as fluorescent biomarkers because of (1) their highly favorable photophysical properties, (2) high chemical stability, (3) low dark toxicity (for live cell and animal imaging), (4) easy tuning of their photophysical and biological properties by varying the nature of the substituents, coordinated metal ion and axial ligand(s), and (5) their ready conjugation to biomolecules such as peptides and nucleic acids.

BRIEF DESCRIPTION OF THE DRAWINGS

Drawings

FIG. 6 depicts photographs of gel chromatograms on polyacrylamide (a-c) and agarose (d, e) gels after electrophoresis of PCR with phthalocyanine labels.

MODES FOR CARRYING OUT THE INVENTION

Figure 1:
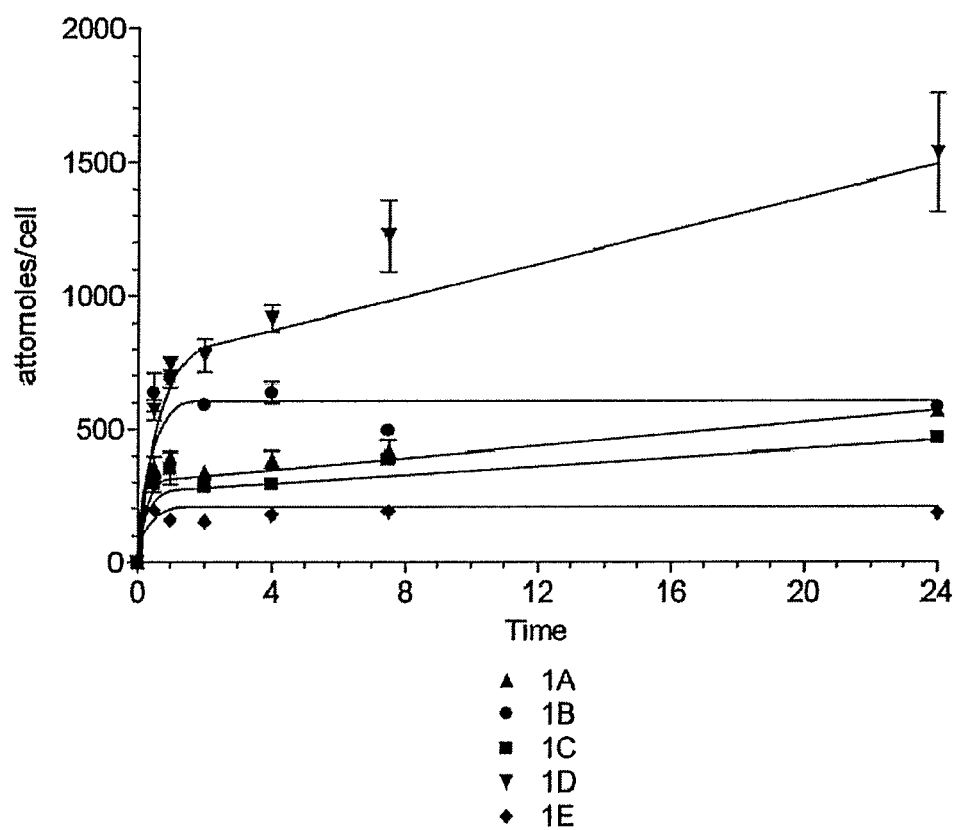
FIG. 1 depicts the cellular uptake of compounds 1A-1E as a function of time.

We have synthesized a number of novel, chemically robust, near-infrared (near-IR) fluorophores. The general structure of the asymmetric novel compounds is:

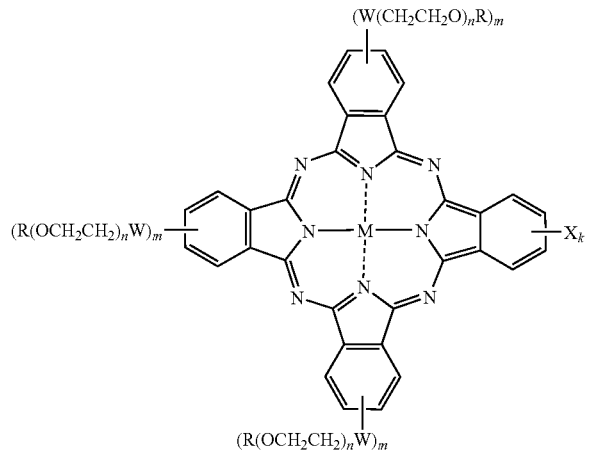

wherein:
M is selected from the group consisting of 2H, Zn, Ni, Cu, $SnY_2$, Pd, Pt, AlY, GaY, $SiY_2$, V(O) and CoY;
Y is selected from the group consisting of F, Cl, Br, I, OR, OH, SR, —CCR, C≡CR, OPh, $CH_3$, $C_2H_5$, Pr, i-Pr, Bu, i-Bu, Ph and mixtures thereof;
n is 3, 4, 5, or 6; where the n's are always the same;
m is 1 or 2; where the m's are always the same;
k is 1 or 2;
R is selected from the group consisting of $CH_3$, H, $CH_2CH_3$, iPr, iBu, and $SO_3H$; where the R's may be the same or different;
W is selected from the group consisting of O, S, and NH; where the W's are always the same;
X is selected from the group consisting of —O-Ph-$CO_2H$, $NH_2$, $NO_2$, $SO_3H$, $O(CH_2CH_2)_nOR$, —N═C═S, —NH (CO)$CH_2Cl$, —NH(CO)$CH_2Br$, —NH(CO)$CH_2I$, —NH (CO)$NHNH_2$, —OPh-(CO)H, —O-Ph-(CO)$NHNH_2$, and —NHCO$(CH_2)_j$COOH.
j is 2-12;
R' is selected from the group consisting of $CH_3$, H, $CH_2CH_3$, iPr, iBu, and $SO_3H$;
and
X and R(OCH$_2$CH$_2$)$_n$W may not be the same.

These phthalocyanines (Pcs) macrocycles are excellent fluorescent biomarkers because they absorb and fluoresce in the near-IR region. Furthermore, because the novel Pcs have high photochemical stabilities, they also afford ultra-sensitive analysis, and long imaging times.

We have synthesized symmetrically and asymmetrically-substituted metallo-Pcs. In addition, we have measured the photophysical properties of the novel dye systems and bioconjugates. Further we have determined the dark- and photo-toxicity of the novel dye systems and bioconjugates. These dye systems and their bioconjugates may be used for cells and DNA analysis, DNA sequencing, and small animal imaging.

New Compounds

The novel phthalocyanine ("Pc") compounds include, among others, the following general structures; several examples of such novel Pcs have been synthesized.

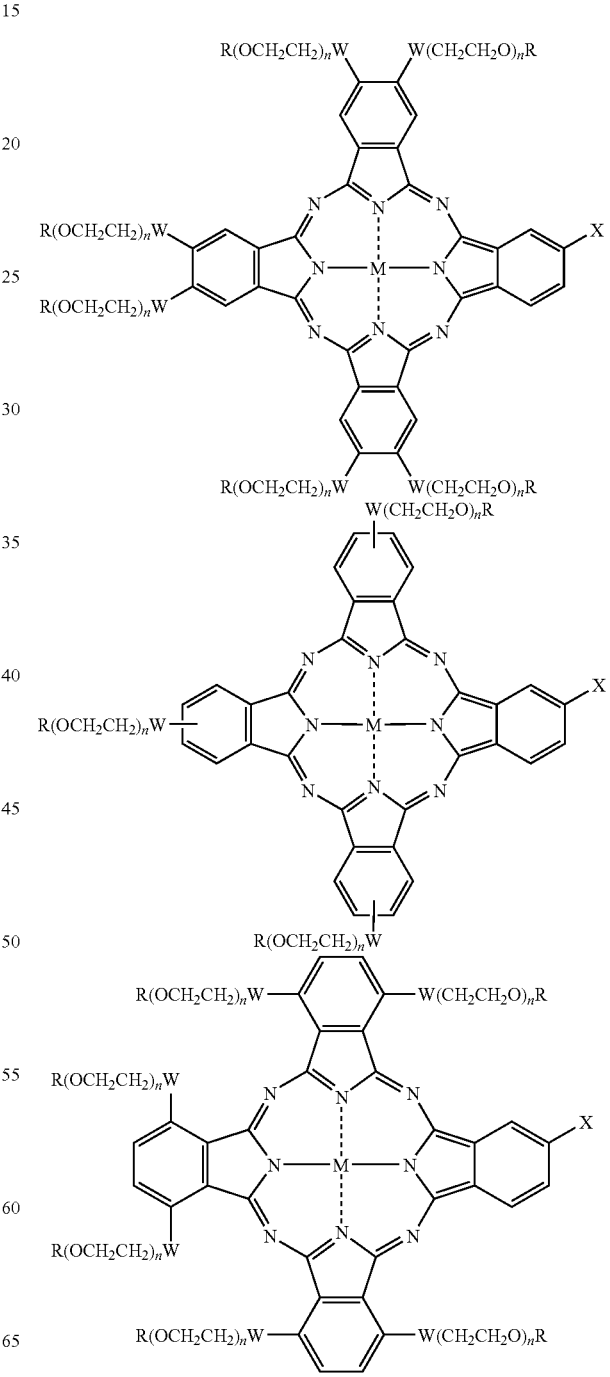

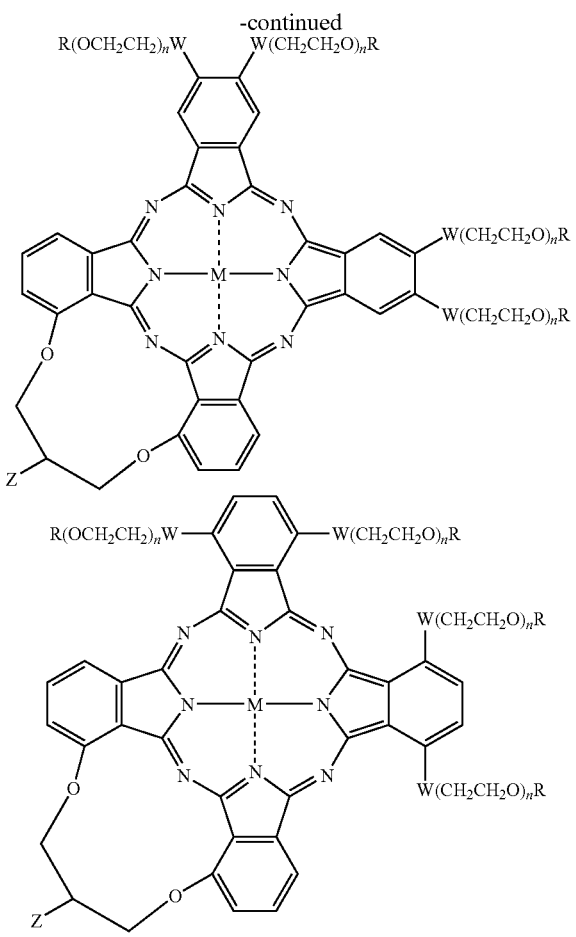

wherein:

Z is selected from the group consisting of NR"R''', SR" and OR", where R" and R''' are selected from the group H, Ph-CO$_2$H, O, ((CH$_2$)$_n$)$_m$OR, C=S, (CO)CH$_2$Br, (CO)CH$_2$I, (CO)NHNH$_2$, Ph(CO)H, Ph(CO)NHNH$_2$, and CO(CH$_2$) COOH, where, R" and R''' may be different or the same.

The novel phthalocyanine compounds have, for example, been synthesized by one of two convenient syntheses using hexamethyldisilazane ("HMDS"), DMF or 1,8-diazabicyclo [5.4.0]-undec-7-ene ("DBU") as condensing reagents in an alcohol (e.g., n-pentanol).

One synthetic method began with 5-amino-1,3-diiminoisoindoline, which was synthesized from 4-aminophthalonitrile by passing gaseous ammonia through methanolic solution of the 4-aminophthalonitrile in the presence of sodium methoxide. 4-(4-alkoxycarbonylphenyloxy)-phthalonitrile was prepared by the nucleophilic substitution reaction of the nitro group in 4-nitrophthalocyanine with 4-hydroxybenzoates. To insert different metals into the complex an appropriate metal acetate, metal halide, such as the chloride, bromide or iodide, or other simple metal salt was used. For example for Zn phthalocyanine, a mixture of triethylene glycol phthalocyanine, appropriate 5-amino-1,3-diiminoisoindoline or 4-(4-methoxycarbonylphenyloxy)-phthalonitrile, and anhydrous zinc acetate was dissolved in a mixture of HMDS and DMF, and kept at 100° C. under argon until the reaction mixture became dark blue (Scheme 1). The solvents were removed in vacuo, the residue was stirred with methanol and evaporated to dryness. The mixture was separated on silica gel with methylene chloride-methanol mixture as an eluent. The syntheses of phthalocyanines with carboxy groups was based on the hydrolysis of an ester group by LiOH in THF/methanol. For complexes in which M was a species other than Zn, such as Ni, Cu, SnY$_2$, Pd, Pt, AlY, GaY, SiY$_2$, V(O) or CoY, an appropriate acetate or chloride was used in place of the Zn(OAc)$_2$ in this reaction scheme. The R-groups were altered by using a different starting phthalonitrile. Likewise the X-groups were altered by starting with another phthalonitrile, or an isoindoline, or another compound with available nitrogen-containing functionalities, so that condensation to a phthalocyanine occurred. For example, as shown in reaction scheme 1, the reactants may include a phthalonitrile and an isoindoline.

A mixture of a phthalonitrile, such as 4-(4-pentyloxycarbonyl phenoxy)phthalonitrile and another phthalonitrile, such as 4-(2-(2-(2-methoxy ethoxy)ethoxy)ethoxy)phthalonitrile), an anhydrous metal salt, such as zinc acetate, and dry n-pentanol was heated to 65° C. under argon. DBU was added dropwise to the mixture, which was then refluxed for 24-48 hours. The solvents were removed in vacuo, and the residue was purified by column chromatography (dichloromethane/methanol, 97:3). Hydrolysis was required in some cases, such as for the synthesis of compound 1C (see below).

For example to prepare compound 1C (see below), a solution of pentyl ester of 1C in THF was added dropwise to a solution of LiOH.H$_2$O in 70% aqueous methanol (10 mL). The mixture was stirred at 60° C. for 17 hrs. The organic solvents were removed in vacuo, and the aqueous phase was brought to pH=2 with 1M HCl. The resultant precipitate was centrifuged and separated on a silica gel column using a dichloromethane/methanol mixture (97:3) as eluent.

A modification of this general method is shown below in Scheme 2. This approach allowed us to synthesize tethered phthalocyanines. Scheme 2 outlines a strategy using a Boc-serinol-tethered bisphthalonitrile as one of the starting compounds. In general the central metal used in this synthesis was a Mg salt. Once the final compound was formed, we were able to wash the Mg from the complex and replace it with a metal such as Ni, Cu, SnY$_2$, Pd, Pt, AlY, GaY, SiY$_2$, V(O) and CoY, using a salt such as a chloride or an acetate. The R-groups were modified in the same manner as described above in the general procedure. Sulfur- or oxygen-protected compounds may be used in place of the nitrogen-Boc protected ligand when making other tethered phthalocyanine compounds.

Scheme 2

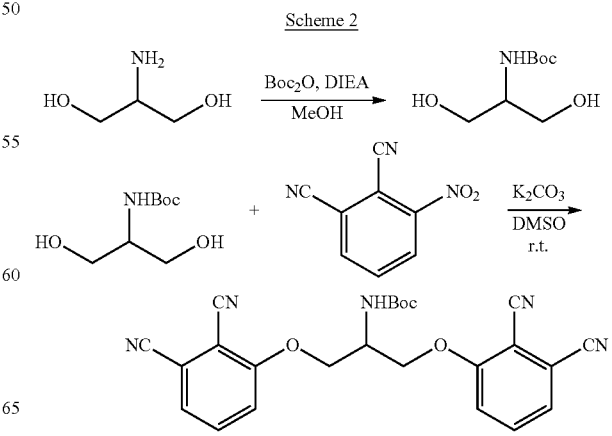

-continued

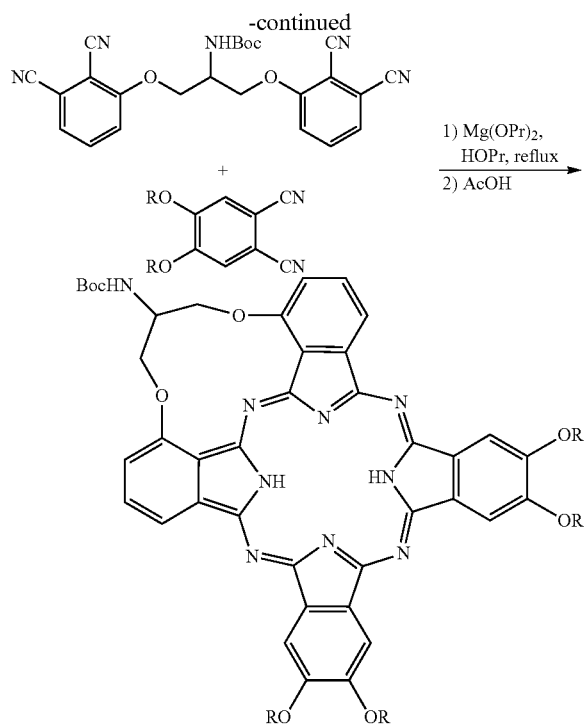

A series of Pc complexes with the structures listed below were used to demonstrate the effectiveness of the complexes in the novel methods.

Compound 1 (A-E)

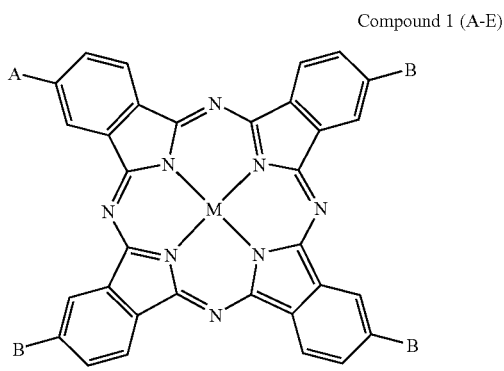

In Compound 1A, M is Zn; A and B are —O(CH$_2$CH$_2$O)$_3$CH$_3$.

In Compound 1B, M is SnCl$_2$; A and B are —O(CH$_2$CH$_2$O)$_3$CH$_3$.

In Compound 1C, M is Zn; A is —OPhCOOH; B is —O(CH$_2$CH$_2$O)$_3$CH$_3$.

In Compound 1D, M is Zn; A is —NH$_2$; B is —O(CH$_2$CH$_2$O)$_3$CH$_3$.

In Compound 1E, M is Zn; A and B are —OPhCOOH.

Figure 8:
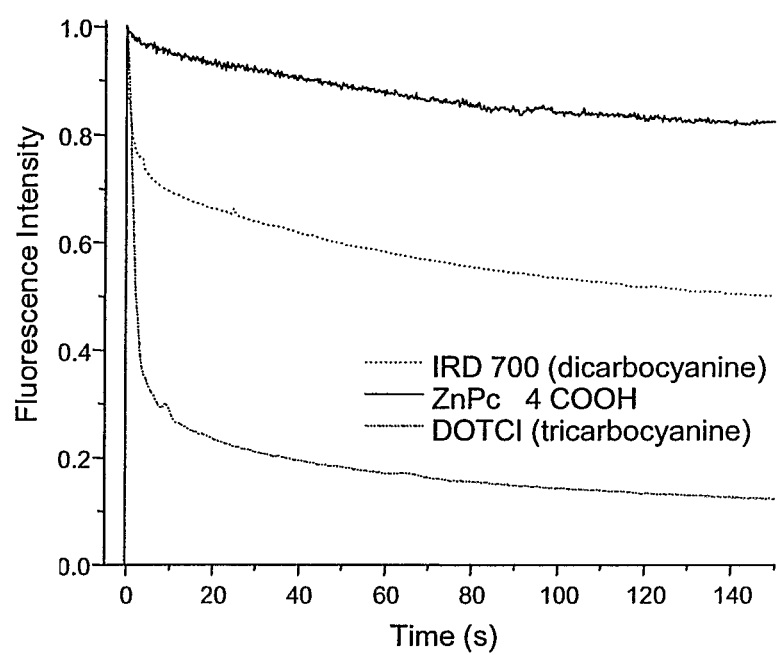
FIG. 8 depicts fluorescence intensity versus time for DOTCI and IRD700 and Zn-Pc.

We have discovered that metallo-Pc systems are highly useful as fluorescent reagents because of (1) their highly favorable photophysical properties, (2) high chemical stability, (3) low dark toxicity (for live cell and animal imaging), (4) easy tuning of their photophysical and biological properties by varying the nature of the substituents, coordinated metal ion and axial ligand(s), and (5) their ready conjugation to biomolecules such as peptides and nucleic acids. We have developed methods to label cells, proteins, mitochondria, DNA, and other biological entities with these Pc-based molecules. The particular Pc-derivative is contacted with the cell, biomolecule, or other biological entity. These compounds are taken up by the cells quickly. FIG. 1 shows amount of compounds 1A-1E that were taken up by cells as a function of time. Further, these compounds are not easily bleached, as shown in FIG. 8, where this figure depicts the fluorescence intensity as a function of time from the ZnPc, in comparison with other dyes. As can be seen, from FIG. 8, the ZnPc's fluorescence is stable while the fluorescence of the other dyes diminishes rapidly. Once the Pc-compound is in the cell, it will either attach to a part of the cell, such as the mitochondria, or remain within the cell unbound. In some instances, chemical reactions occur, and conjugation between the Pc-derivative and a biological molecule of interest results, such as when compound 1C, 1D or 1E attaches to an oligonucleotide.

We also have discovered other novel phthalocyanines and tetraazaporphrins, that, depending on the central metal and other constituents, may be used as dyes, PDT reagents, for bioanalytical studies, or for DNA analysis. The complexes have very high photon emission yields in the near-IR region. For example, structure 1E, where M is Zn and A and B are (—O-Ph-CO$_2$H), has a fluorescence yield of about $10^5$ photons/molecule, while a typical commercially available dye, such as tricarbocyanines, produces only approximately 10 photons/molecule. Such improvements in photon yields for a chemically robust, near-IR fluorophore, will greatly enhance both bioimaging and bioanalysis. We have developed new methods in which the appropriate Pc-based molecule is placed in contact with DNA, a cell, a protein, or other biological entity, to detect cell, the DNA, or allow bio-analysis of the target species. Furthermore, we have developed new methods of selective cell destruction via PDT technology by introducing the appropriate Pc-derived complex into a cell and then exposing the cell to near-IR radiation.

There is also a more general need to develop new diagnostic tools, for applications such as labeling or staining biological entities, through fluorescence. The dyes in common use for these applications have certain drawbacks, as described above. Our novel dyes readily attach to primers and terminators of DNA and also readily conjugate with other biological entities, such as proteins, peptides, nucleic acids, nucleotides, and oligonucleotides. The novel dyes and their conjugated complexes withstand thermal and chemical conditions typically used in preparing oligonucleotides for immunoassays and other biological assays.

We have successfully loaded compounds 1A and 1C in human larynx cells in vitro, and thereafter observed their fluorescence. For comparison, in separate experiments, we loaded ERTracker dye or MiroTracker dye into the larynx cells. The results showed that compounds 1A and 1C co-located in mitochondria or endoplasmic reticulum.

Molecular Labeling and Sequencing

This invention also provides new methods for labeling molecules, such as oligonucleotides used in DNA sequence analysis or DNA diagnostic applications. The dye must withstand thermal and chemical conditions used in preparing oligonucleotides for analysis. We have generated novel phthalocyanine derivatives that fulfill these requirements.

Photodynamic Therapy

Many of the novel phthalocyanine derivatives are light-toxic. These light-toxic compounds may be used as photo-sensitizers in photodynamic therapy ("PDT"). When living tissue is treated with the novel Pc-derivative the cells become activated when exposed to radiation in the near-IR region. The cell or tissue is then selectively destroyed. While not wishing to be bound by this theory, it is believed that the interaction between the light and the Pc-compound produces singlet oxygen, which is believed to kill the tissue or cells. When a Pc-based compound is bound to mitochondria or endoplasmic reticulum in a cell and subsequently exposed to actinic light, it is believed that the reactive in situ singlet oxygen causes cell death via apoptosis. Unlike necrosis, apoptosis is an orderly process that does not provoke an immune system response. Killing unwanted tissue, e.g., tumor tissue via apoptosis, is preferred over necrosis, as it will generally produce fewer unwanted consequences for the patient. Photodynamic therapy may be used in treating macular degeneration, some skin and throat cancers, and some bacterial and viral pathogens.

We have discovered a substantial improvement in PDT cell destruction by contacting said target cells with the appropriate novel compound, e.g. compound 1A or 1C (or to a lesser extent, 1E) and light. This method has advantages over other methods now in use because the reagents have a much longer dark shelf life than seen with other PDT-compounds. Further, since these novel complexes absorb in the near-IR, they can target tissue or cells at greater depth than with those PDT-active reagents that are activated in the visible region, since near-IR penetrates tissue deeper than visible light.

Other Uses

The compounds may be used for in vivo imaging and real-time monitoring of tumor progression and metastasis.

Compounds with relatively low dark cytotoxicity and high cytotoxicity following near-IR photoactivation may be used for targeted cancer therapy.

The compounds with low cytotoxicity in the near-IR range can be used in bioimaging, for example, to track and visualize cellular movements (e.g. angiogenesis; cancer progression and metastasis; inflammation) or therapeutic effects by utilizing near-IR fluorescently labeled probes to impart molecular specificity to these images. Hemoglobin (an absorber of visible light), water, and lipids (an absorber of IR light) all have low absorption coefficients in the near-IR region. Therefore, optical imaging of these dye systems in the near-IR is ideal for maximizing deep tissue (up to 10-15 cm) visualization of fluorescent probes, while minimizing tissue-associated autofluorescence.

Example 1

A method for the synthesizing tethered-phthalocyanines is outlined in Scheme 2 below. The R-groups are selected from the group consisting of $CH_3$, H, $CH_2CH_3$, iPr, iBu, and $SO_3H$; where the R's may be the same or different. In addition, optional cyclization using one or more of the functional groups may allow for easier separation of products with differing number of anions by ion exchange chromatography. This general approach can yield either symmetrically or unsymmetrically substituted phthalocyanines. Sulfur- or oxygen-protected compounds may be used in place of the nitrogen-Boc protected ligand when making other tethered phthalocyanine compounds.

Example 2

N-Boc-Serinol

N,N-diisopropylethylamine (DIEA; 10.3 mL, 59 mmol, 1.1 equiv) was added to serinol (4.88 g, 54 mmol, 1 equiv) in 10 mL methanol. A solution of di-t-butyl dicarbonate (12.9 g, 59 mmol, 1.1 equiv.) in 5 mL methanol was then added to the original solution. The reaction was exothermic and evolved gas. The reaction appeared to be complete after 15 min. (as determined by TLC analysis in 9:1 $CHCl_3$:$CH_3OH$ with ninhydrin stain). The solvent was then removed at reduced pressure, and the crude material was purified by flash chromatography, using $CHCl_3$:$CH_3OH$ (first at a 9:1 ratio and then at a 85:15 ratio), to yield 7.18 g (72% yield) of white, flaked crystals. [$R_f$: 0.35 (5:1 $CHCl_3$:$CH_3OH$); melting point 85-86° C.; $^1H$ NMR (200 MHz, $CDCl_3$) δ 5.25 (br d, J=5.6, 1H, NH), 3.9-3.65 (m, 5H, (—$CH_2$)$_2$CH—), 2.62 (t, J=5.6, 2H, OH), 1.45 (s, 9H, C($CH_3$)$_3$)].

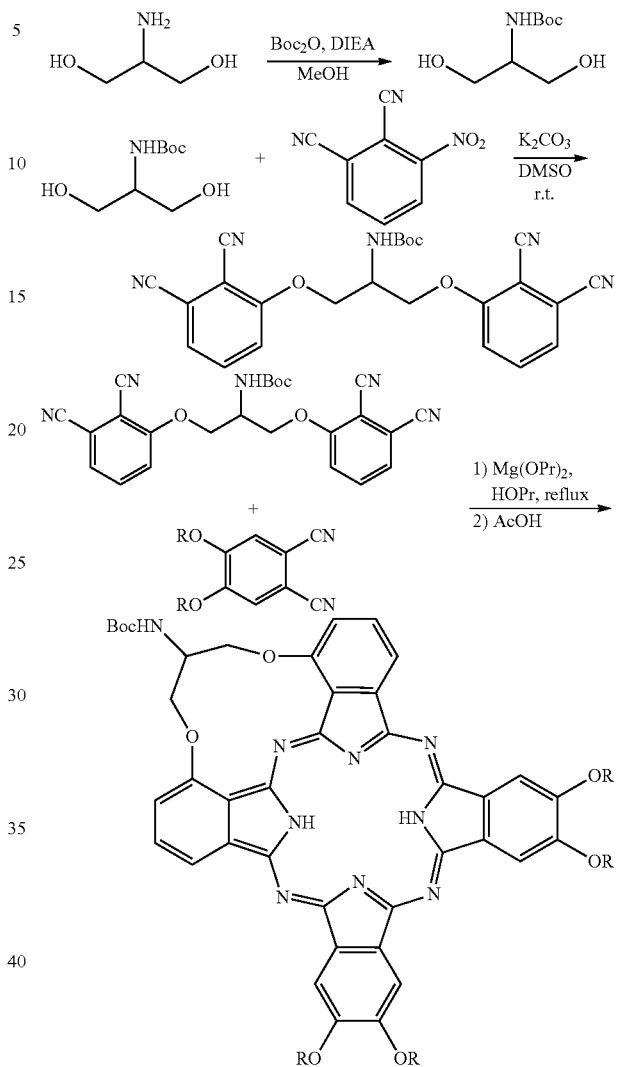

Example 3

To prepare the bis-phthalonitrile used in scheme 2, the nitrogen of serinol was Boc-protected, and the serinol was then reacted with 3-nitrophthalonitrile on a multi-gram scale, to give the desired tethered bis-phthalonitrile, in 70% yield.

Example 4

Synthesis of Serinol Bisphthalonitrile

A mixture of serinol (45.8 mg, 0.50 mmol, 1 equiv.), 3-nitrophthalonitrile (258.1 mg, 1.5 mmol, 2.5 equiv.) and $K_2CO_3$ (277.4 mg, 2.0 mmol, 4 equiv.) in 3 mL DMSO was stirred at room temperature and monitored periodically by TLC (9:1 benzene:$CH_3CN$). The reaction mixture changed from orange to brown as the reaction occurred. After 90 h, the reaction mixture was heated to 70° C. TLC analysis showed the gradual disappearance of 3-nitrophthalonitrile over the next 8.5 h. The reaction mixture was partitioned between EtOAc and water, and the two layers were separated. The aqueous layer was extracted with EtOAc. This organic extract was combined with the phase-separated organic layer from the original separation, and then this mixture was washed twice with saturated NaHCO$_3$, twice with water, and once with saturated NaCl. TLC analysis of the crude material showed no ninhydrin positive spot. The crude material was purified by flash chromatography using benzene:CH$_3$CN (95:5) to extract the major UV-active spot.

Example 5

Boc-serinol Bisphthalonitrile

Finely ground K$_2$CO$_3$ (4.32 g, 31.2 mmol, 4 equiv.) was added to N-Boc-serinol (1.45 g, 7.8 mmol, 1 equiv.) in 20 mL DMSO under argon; then 3-nitrophthalonitrile (3.38 g, 19.5 mmol, 2.5 equiv.) was added. The reaction mixture first turned pink, and then orange upon addition of the 3-nitrophthalonitrile. The reaction mixture was stirred at room temperature and monitored periodically by TLC (9:1 benzene:CH$_3$CN). After 72 h, the reaction mixture was partitioned between EtOAc and water. The two layers were separated, and the aqueous layer was extracted 3 times with 50 mL EtOAc. The organic layer from the original partitioning was added to the organic extract. This mixture was then washed twice with 50 mL of saturated NaHCO$_3$, and twice with 50 mL of water, and was then dried over Na$_2$SO$_4$. The solvent was removed at reduced pressure, and the resulting crude orange solid was recrystallized from methanol/water to give 2.43 g (70% yield) of a slightly pink/tan solid. [R$_f$: 0.25 (9:1 benzene:CH$_3$CN); melting point 167-169° C.; $^1$H NMR (200 MHz, CD$_3$CN) δ 7.85-7.4 (m, 6H, ArH), 5.76 (br s, 1H, NH), 4.39 (s, 5H, (—CH$_2$)$_2$CH—), 1.42 (s, 9H, C(CH$_3$)$_3$).]

Example 6

Synthesis of Boc-serinol-Pc(OMe)$_4$

A flask containing magnesium turnings (23 mg, 0.95 mmol, 3 equiv./Pc ring) in 10 mL n-propanol was heated to reflux under argon. A small crystal of I$_2$ was added to initiate the reaction. The mixture was heated at reflux and stirred for 20 h. Boc-serinol-bisphthalonitrile (133.5 mg, 0.30 mmol, 1 equiv.) and 4,5-dimethoxyphthalonitrile (113.0 mg, 0.60 mmol, 2 equiv.) were added. The color of the reaction progressed from yellow to light green to very dark green. After 24 h, the solvent was removed by reduced pressure. Our initial attempt to purify this product by column chromatography using silica gel and CH$_2$CO$_2$, CHCl$_3$, and/or CH$_3$OH was unsuccessful. The recollected material was then dissolved in 10 mL of CH$_2$Cl$_2$, to which 10 mL of glacial acetic acid was added. After 1 h, the solution was poured over a mixture of ice and concentrated NH$_4$OH. The two layers were separated and the aqueous layer was extracted with CH$_2$Cl$_2$ until the extracts were clear. The combined organic layers were dried over Na$_2$SO$_4$, and then the solvent was removed by reduced pressure.

Example 7

4-(4-Methoxycarbonylphenyloxy)-phthalonitrile was prepared by the nucleophilic substitution reaction of the nitro group in 4-nitrophthalocyanine using 4-hydroxybenzoate. In order to prepare compounds 1C-1D, wherein M is Zn, a mixture of triethylene glycol containing phthalocyanine and the appropriate 4-(4-methoxycarbonylphenyloxy)-phthalonitrile or 5-amino-1,3-diiminoisoindoline, and anhydrous zinc acetate was dissolved in a mixture of HMDS and DMF, and kept at 100° C. under argon until the reaction mixture became dark blue. The solvents were removed in vacuo; then the residue was stirred with methanol, and the mixture was evaporated to dryness. The product was then separated on silica gel with a methylene chloride-methanol mixture as an eluent. In addition, to complete the syntheses of 1C, hydrolysis of an ester group by LiOH in THF/methanol mixtures was required.

Scheme 1

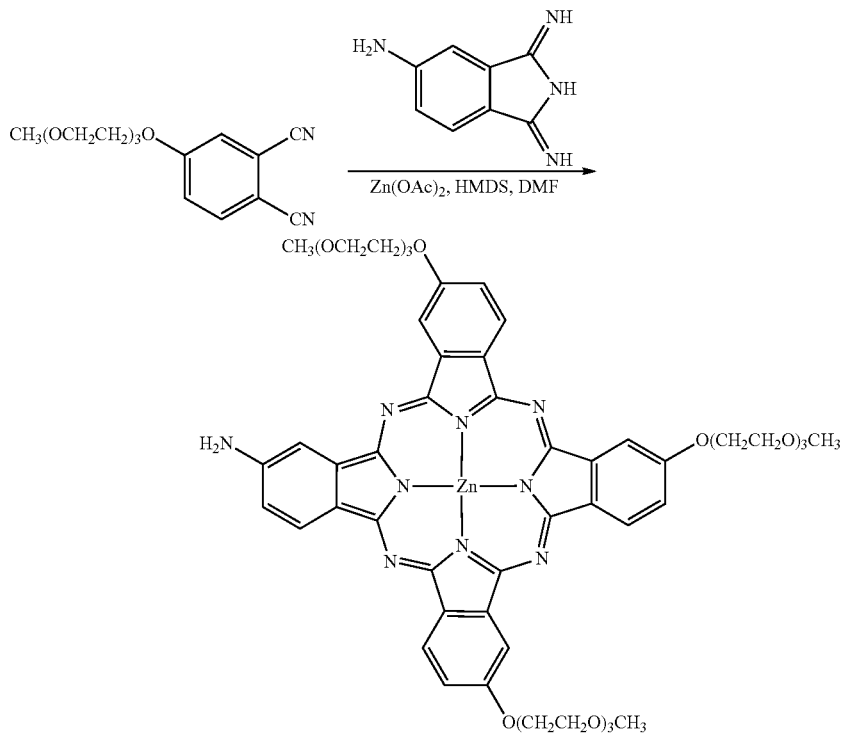

-continued

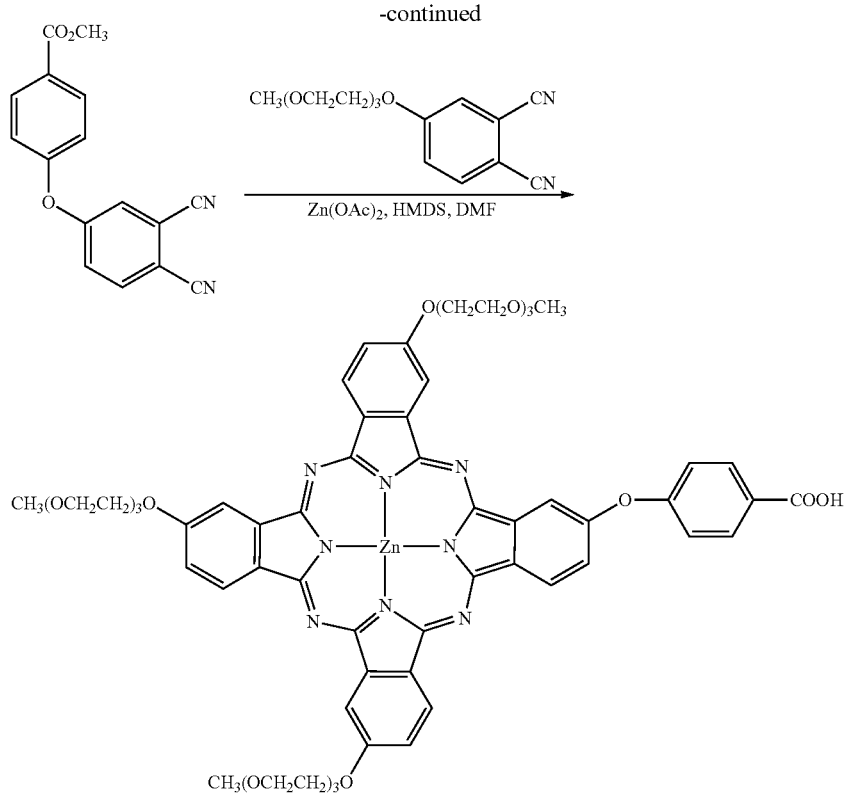

Example 8

Preparation of tin-containing Pcs with HMDS failed to yield a product. However, using a mixture of DBU and n-pentanol as solvent facilitated the synthesis of 1B (wherein M was $SnCl_2$). Phthalonitrile and stannous chloride were mixed in anhydrous n-pentanol, and the mixture was heated at 65° C. for 30 min. DBU was added, and then the mixture was refluxed for 18 hr. After cooling, the solvents were removed in vacuo. The mixture was eluted through the CSX-2 (Argonaut) column with a mixture of methylene chloride and methanol. The resulting product was then separated by flash-chromatography on silica gel (methylene chloride-methanol eluent). [$^1$H NMR (δ, ppm, DMSO-d$^6$): 9.28 (m, 2H), 9.05 (m, 2H), 8.71 (m, 2H), 8.28 (m, 2H), 7.75-8.05 (m, 4H), 4.52 (br., 8H), 4.00 (br., 8H), 3.25-3.8 (br., 32H), 3.22 (br. s, 6H), 3.18 (s, 6H). MS (MALDI) m/z calcd for $C_{60}H_{72}ClN_8O_{16}Sn$ (M-Cl$^+$) 1315.42, found 1315.71]

Example 9

Symmetric compounds (1A, 1E, wherein M was Zn) were prepared by the same method as described in Example 7, except that for compound 1A, 3-(2-(2-(2-methoxy)ethoxy)ethoxy)phthalonitrile was used in the initial step, and for compound 1E, 4-(4-pentyloxycarbonylphenoxy)phthalonitrile was used in the initial step. In addition, to complete the syntheses of 1E, hydrolysis of an ester group by LiOH in THF/methanol mixtures was required.

Example 10

The structures of compounds 1A-1E, the syntheses of which were described in Examples 7-10 above, are:

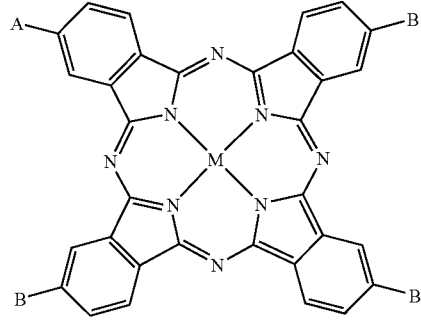

wherein:

In Compound 1A M was Zn; A and B were —$O(CH_2CH_2O)_3CH_3$.

In Compound 1B M was $SnCl_2$; A and B were —$O(CH_2CH_2O)_3CH_3$.

In Compound 1C M was Zn; A was —OPhCOOH; B was —$O(CH_2CH_2O)_3CH_3$.

In Compound 1D M was Zn; A was —$NH_2$; B was —$O(CH_2CH_2O)_3CH_3$.

In Compound 1E M was Zn; A and B were —OPhCOOH.

Example 11

Synthesis of 1C

A mixture of 4-(4-pentyloxycarbonylphenoxy)phthalonitrile (0.670 mg, 2.0 mmol) and 4-(2-(2-(2-methoxyethoxy)ethoxy)ethoxy)phthalonitrile (1.740 g, 6.0 mmol), anhydrous zinc acetate (0.732 g, 4.0 mmol) and dry n-pentanol (20 mL)

was heated to 65° C. under argon. DBU (10.0 mmol) was added dropwise to the mixture, which was then refluxed for 24 hours. The solvents were removed in vacuo, and the residue was purified by column chromatography (dichloromethane/methanol, 97:3). The fractions were combined and evaporated to dryness and the residue, dissolved in THF, was added dropwise to a solution of LiOH.H$_2$O (42 mg, 1 mmol) in 70% aqueous methanol (10 mL). The mixture was then stirred at 60° C. for 17 hrs. The organic solvents were removed in vacuo. The remaining solution was acidified to pH 2 using 1M HCl. The precipitate that resulted was centrifuged and then separated on a silica gel column using a dichloromethane/methanol mixture (97:3) as an eluent to give 1C in a 35% yield. [$^1$H NMR (δ, ppm, DMSO-d$^6$): 8.97 (m, 2H), 8.82 (m, 2H), 8.62 (m, 1H), 8.53 (m, 1H), 8.36 (m, 2H), 8.18 (m, 2H), 7.84 (m, 1H), 7.45-7.70 (m, 5H), 7.75-8.05 (m, 4H), 4.62 (m, 6H), 4.10 (m, 6H), 3.86 (m, 6H), 3.74 (m, 6H), 3.64 (m, 6H), 3.51 (m, 6H), 3.28 (m, 6H), 3.26 (s, 3H). MS (MALDI) m/z calcd for $C_{60}H_{63}N_8O_{15}Zn$ (MH$^+$) 1199.370, found 1199.380.]

Example 12

5-Amino-1,3-diiminoisoindoline was synthesized by passing gaseous ammonia through methanolic solution of 4-aminophthalonitrile in the presence of sodium methoxide.

Example 13

Synthesis of 4-(4-pentyloxycarbonylphenoxy)phthalonitrile

A mixture of 4-nitrophthalonitrile (1.00 g, 7 mmol), pentyl 4-hydroxybenzoate (1.45 g, 7 mmol) and dried potassium carbonate (6.38 g, 46.2 mmol) in anhydrous DMF (50 mL) was stirred overnight at 85° C. under argon. After cooling to room temperature, the mixture was diluted with ethyl acetate (60 mL) and water (40 mL). The organic layer was separated, and the aqueous phase was extracted with ethyl acetate (2×50 mL). The combined organic layers were washed with a saturated solution of NaHCO$_3$ (40 mL), brine (40 mL) and dried over anhydrous sodium sulfate. The solvents were removed in vacuo, and the crude product was purified by column chromatography on silica gel using a dichloromethane/acetonitrile mixture (20:1) as an eluent to give the product in 85% yield. [$^1$H NMR (δ, ppm, CDCl$_3$): 8.15 (d, 2H, J=8.7 Hz), 7.77 (d, 1H, J=8.7 Hz), 7.35 (d, 1H, J=2.3 Hz), 7.30 (d, 1H, J=8.7 Hz), 7.12 (d, 2H, J=8.7 Hz), 4.34 (2H, t, OCH$_2$, J=6.7 Hz), 1.79 (m, 2H, CH$_2$), 1.42 (m, 4H, CH$_2$CH$_2$), 0.94 (t, 3H, J=7 Hz, CH$_3$).]

Example 14

Synthesis of 4-(2-(2-(2-methoxyethoxy)ethoxy)ethoxy)phthalonitrile)

A mixture of 4-nitrophthalonitrile (1.73 g, 10 mmol), triethylene glycol monomethyl ether (1.52 g, 10 mmol) and dried potassium carbonate (2.76 g, 20 mmol) in anhydrous DMF (15 mL) was stirred overnight at ambient temperature under argon. The solvents were removed in vacuo, and the crude product was purified by column chromatography on silica gel using dichloromethane/methanol mixture (97:3) as an eluent to give the product in 45% yield. [$^1$H NMR (δ, ppm, CDCl$_3$): 7.70 (d, 1H, J=8.7 Hz), 7.31 (d, 1H, J=2.5 Hz), 7.23 (dd, 1H, J=8.7 Hz, J=2.5 Hz), 4.22 (m, 2H), 3.88 (m, 2H), 3.6-3.75 (m, 6H), 3.53 (m, 2H), 3.37 (s, 3H).]

Example 15

To prepare compound 1D, a mixture of 4-aminophthalonitrile (0.05 mmol) and 4-(2-(2-(2-methoxyethoxy)ethoxy)ethoxy)phthalonitrile) (0.15 mmol), anhydrous zinc acetate (37 mg, 0.2 mmol) and dry n-pentanol (20 mL) was heated to 65° C. under argon. DBU (2.5 mmol) was added dropwise to the mixture, which was refluxed for 24 hours. The solvents were removed in vacuo, and the residue was purified by column chromatography (dichloromethane/methanol, 97:3) to give a 23% yield. [$^1$H NMR (δ, ppm, DMSO-d$^6$): 8.90 (br., 4H), 8.5 (br., 4H), 7.3-7.7 (br., 6H), 6.35 (br., 2H), 4.55 (br., 8H), 4.02 (br., 8H), 3.30-3.85 (br., 32H), 3.27 (br., 6H), 3.25 (s, 3H), 3.21 (s, 6H). MS (MALDI) m/z calcd for $C_{53}H_{61}N_9O_{12}Zn$ (MH$^+$) 1079.373, found 1079.738.]

Example 16

To prepare 1C (wherein M was Zn), by HMDS-induced synthesis, a mixture containing 4-(4-methoxycarbonylphenyloxy)phthalonitrile, 4-(4-pentyloxycarbonylphenoxy)phthalonitrile in triethylene glycol and anhydrous zinc acetate was dissolved in a mixture of HMDS and DMF, and kept at 100° C. under argon until the reaction mixture became dark blue. The solvents were removed in vacuo, and the residue was stirred with methanol and evaporated to dryness. The mixture was separated on a silica gel with a methylene chloride-methanol mixture (97:3) as eluent. [$^1$H NMR (δ, ppm, DMSO-d$^6$): 8.97 (m, 2H), 8.82 (m, 2H), 8.62 (m, 1H), 8.53 (m, 1H), 8.36 (m, 2H), 8.18 (m, 2H), 7.84 (m, 1H), 7.45-7.70 (m, 5H), 7.75-8.05 (m, 4H), 4.62 (m, 6H), 4.10 (m, 6H), 3.86 (m, 6H), 3.74 (m, 6H), 3.64 (m, 6H), 3.51 (m, 6H), 3.28 (m, 6H), 3.26 (s, 3H). MS (MALDI) m/z calcd for $C_{60}H_{63}N_8O_{15}Zn$ (MH$^+$) 1199.370, found 1199.380.]

Cell-Staining, Labeling and Sequencing

Example 17

Some of the hydrophilic phthalocyanines (Pcs) of general formula 1, where M is Zn or SnCl$_2$; A is an amino, 4-carboxyphenoxy or triethyleneglycol substituent; and B is a triethyleneglycol chains (terminated with methoxy groups), have been synthesized. See examples 7 & 8. These Pcs are readily taken up by human cells, localizing in the mitochondria or lysosomes, as shown in FIG. 1, which depicts the cellular uptake of Pcs of the general formula 1, as a function of time.

Example 18

We found that the fluorescence lifetimes of the dyes may be controlled by introducing different metals (M) to the chromophore. Since the dye structures of a set of chromophores, modified with different metals, were otherwise similar, the dyes were found to migrate through a capillary gel column at approximately the same rate, alleviating the need for post-electrophoresis mobility corrections when doing DNA analysis. For example, we found fluorescent lifetimes of 2.9 ns for compound 1E (wherein M was Zn), 3.5 ns for compound 1E (replacing M with Ga(Cl)), and 5.2 ns for compound 1E (replacing M with Al(Cl)).

Example 19

Fluorescence lifetimes were determined using time-correlated single photon counting (TCSPC) on a Fluotime 200

(Picoquant, Berlin Germany). The excitation source was a 680 nm pulsed diode laser (PDL 800, Picoquant). Since rotational diffusion could lead to distortion of the fluorescence decay, a polarizer was inserted into the system and set at the magic angle of 54.7°. The spectrometer used a monochromator (ScienceTech 9030) and a photomultiplier tube (PMS 182-M single photon detection). All electronics for TCSPC were situated on a single PC card resident on the bus of the PC, and included a constant fraction discriminator and time-to-digital converter with an instrument response function of ~450 ps (FWHM). Time-resolved data were analyzed using FluoFit software (Picoquant, Berlin Germany). The fluorescence decays of 10-100 nM Pcs in DMSO were collected until 10,000 counts were accumulated in the time channel with the most counts. The decays were then fit to single or multiexponential functions by an iterative reconvolution algorithm using nonlinear least squares.

Below are descriptions of some of the novel compounds used to label mitochondria.

Example 20

We have discovered novel asymmetric hydrophilic phthalocyanines that are readily taken up by cells, localizing in the mitochondria. The phthalocyanines have the general formula:

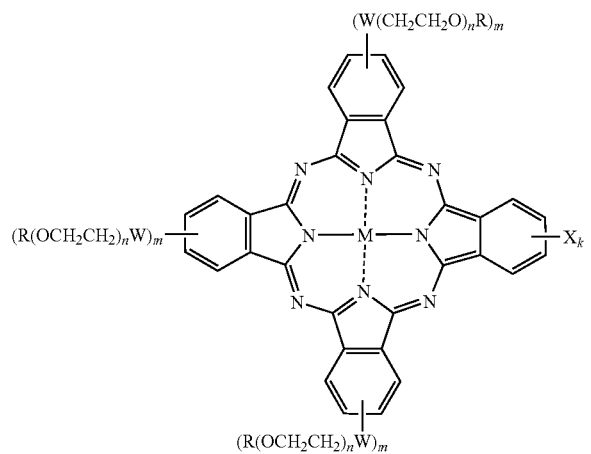

wherein:
M is selected from the group consisting of 2H, Zn, Ni, Cu, $SnY_2$, Pd, Pt, AlY, GaY, $SiY_2$, V(O) and CoY;
Y is selected from the group consisting of F, Cl, Br, I, OR, OH, SR, —CCR, C=CR, OPh, $CH_3$, $C_2H_5$, Pr, i-Pr, Bu, i=Bu, Ph and mixtures thereof;
n is 3, 4, 5, or 6; where the n's are always the same;
m is 1 or 2; where the m's are always the same;
k is 1 or 2;
R is selected from the group consisting of $CH_3$, H, $CH_2CH_3$, iPr, iBu, and $SO_3H$; where the R's may be the same or different;
W is selected from the group consisting of O, S, and NH; where the W's are always the same;
X is selected from the group consisting of —O-Ph-$CO_2$H, $NH_2$, $NO_2$, $SO_3H$, O($CH_2CH_2$)$_n$OR', —N=C=S, —NH(CO)$CH_2$Cl, —NH(CO)$CH_2$Br, —NH(CO)$CH_2$I, —NH(CO)NH$NH_2$, —OPh-(CO)H, —O-Ph-(CO)NH$NH_2$, and —NHCO($CH_2$)$_j$COOH.
j is 2-12;
R' is selected from the group consisting of $CH_3$, H, $CH_2CH_3$, iPr, iBu, and $SO_3H$;
and
X and R(OCH$_2$CH$_2$)$_n$W may be the same or different.

Example 21

Cellular uptake, cytotoxicity and organelle specificity were studied using HEp2 human cells. Cells incubated in the presence of both the asymmetric Pcs 1C, 1D, and the symmetric Pcs 1A, 1B, & 1E, showed rapid cell uptake, and specific organelle affinity, such as to mitochondria and ER. At a 10 μM concentration, the uptake reached its maximum in 1 hr, whereas at a 1 μM concentration the maximum was reached for 1C, 1E (M comprised Zn) in 2 hr. The uptake of compound 1D (1 μM) did not become constant even after 24 hrs, which may have been caused by its partial precipitation in aqueous media. FIG. 1 shows the cellular uptake of compounds 1A-1E as a function of time in these cells.

Photodynamic Therapy

Example 22

The incorporation of hydrophilic ethylene glycol substituents in the outer rim increased dye solubility in aqueous solutions and decreased the degree of aggregation (π-stacking). These compounds had strong absorption at 675-680 nm and fluorescent emission around 690 nm. Incubation of HEp2 cells with the phthalocyanines resulted in rapid cell uptake and specific organelle distribution, even at low concentrations. The metal, its ligand environment and polar ethylene glycol substituents appeared to play an important role in the cell compartmentalization. For example, tin-containing phthalocyanines (1B, M=SnCl$_2$) were deposited into vesicles, while zinc-containing phthalocyanines (1C, M=Zn) were partitioned specifically in mitochondria. The compounds showed high fluorescence and low dark toxicity, making them suitable for cell staining. When exposed to near-infrared light other phthalocyanines showed high toxicity at low concentrations, useful for photodynamic therapy applications.

Example 23

Hydrophilic phthalocyanines (Pcs) bearing tri(ethylene glycol) chains and having carboxylic or amino functionalities (1C, 1D) have been used as cell markers, especially for mitochondria. The disadvantageous stacking of many Pcs may be overcome, for example, by introducing polar ligands such as sulfonic acid or other sterically large acids, attached to the metal of the phthalocyanine. Moreover, such substitution will increase solubility in aqueous media. The zinc-phthalocyanines 1A, 1C-1E have shown strong absorption at 675-680 nm ($\epsilon$=10$^5$ cm$^{-1}$M$^{-1}$) and fluorescence emission around 690 nm, while the absorption of SnCl$_2$ Pcs (1B) appeared at about 710 nm and emission was seen about 720 nm.

Example 24

Intracellular localization: HEp2 cells were loaded overnight with 10 mM of one of the compounds 1A-1E. After loading, ERTracker Blue/White at 100 nM or MitoTracker at 250 nM was added for 30 minutes. Cells were then washed three times with medium and examined using a Zeiss Axiovert 200M inverted fluorescent microscope fitted with a standard DAPI filter set to visualize the ERTracker (excitation 350 nm and Emission 420 nm LP) or a custom filter set (660 nm excitation and 687 nm long pass emission filters) to visualize the novel compounds.

Zn-Pcs showed strong localization to internal membrane compartments such as the ER and mitochondria. This localization was confirmed using commercially obtained organelle-specific stains for these compartments: MitoTracker Green FM for mitochondria and ERTracker Blue/White for endoplasmic reticulum. Cells were loaded overnight with one of the novel compounds and with 250 mM MitoTracker or 100 nM ERTracker. The loading medium was then removed and the cells were washed with a HEPES solution containing the medium. Fluorescence signals were then observed using appropriate filter sets (FITC for MitoTracker and DAPI for ERTracker). Overlapping signals from the organelle tracers and the compounds confirmed ER and mitochondrial localization. The compounds with amino Zn-Pc (1D), tetracarboxylate Zn-Pc (1E), and symmetrical $SnCl_2$ Pc (1B) all showed a punctate staining that was distributed throughout the cells, showing that these compounds did not co-localize to ER or mitochondrial compartments.

Example 25

Apoptosis assays were performed using the dye JC-1 ((5, 5',6,6'-tetrachloro-1,1',3,3'-tetraethyl-benzamidazo-Iocarbocyanin iodide (MitoPT kit Immunochemistry Technologies)). The JC-1 dye is sensitive to mitochondrial membrane potential. When excited with 480 nm light, dye aggregates fluoresce red, while the monomeric form fluoresces green. The dye is sequestered inside intact mitochondria, where it aggregates to produce a red signal. If the mitochondrial membrane potential is lost (as is in early apoptosis), the dye is released from the mitochondria, and then dissociates into monomers which then fluoresce green. By measuring the ratio of red to green fluorescence, it is possible to determine the state of the mitochondrial membrane.

Figure 2:
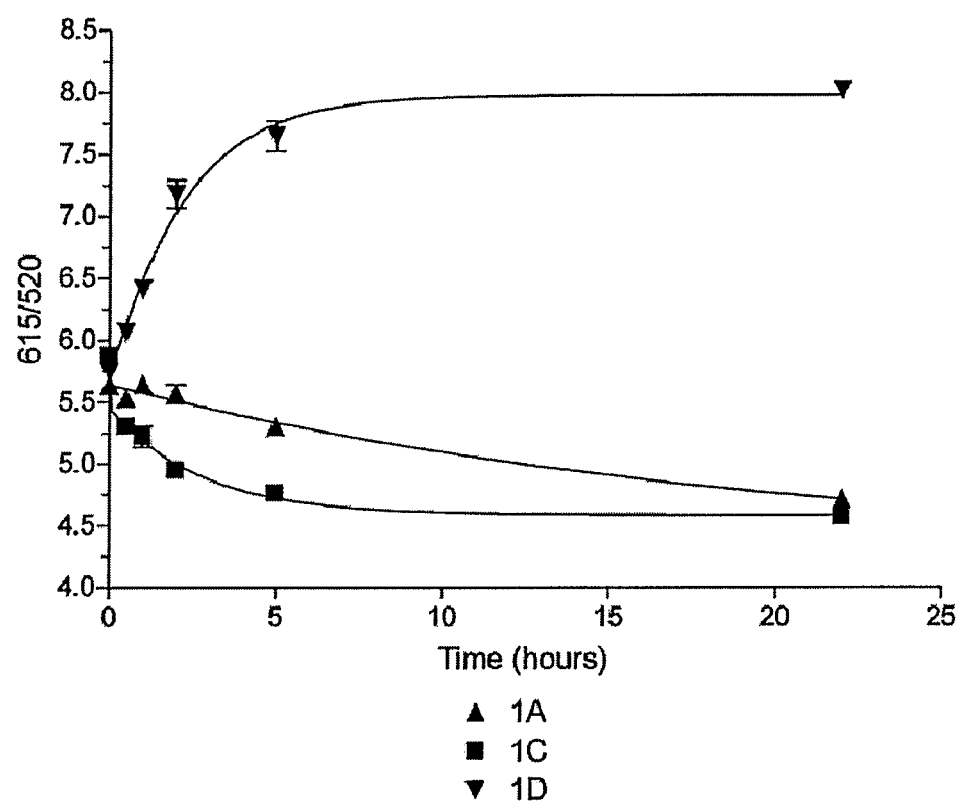
FIG. 2 depicts the change in the ratio of emissions at 615 nm to 520 nm versus time, for compounds 1A, 1C, and 1D.

Cells were loaded with 10 mM compound overnight. The loading medium was then removed and the cells were fed a medium containing JC-1 (as per manufacturer's instructions) and incubated for 15 minutes. The JC-1 loading medium was then removed and the cells washed with growth medium containing 50 mM HEPES pH7.4, and then fed the same growth medium. Cells were then exposed to 610 nm filtered light to provide a light dose of approximately 0.5 J $cm^{-2}$. Fluorescence was then monitored over time. FIG. 2 shows the ratio of red to green (615/520 nm) signal for three of the compounds. Compound 1D did not show any toxicity in the phototoxicity experiments. This lack of toxicity was reflected in the apoptosis assay by a continued increase in the 615/520 signal ratio. On the other hand, compounds 1A and 1C did show a strong phototoxic effect and also show a markedly lower 615/520 signal ratio, a dramatic decrease in red fluorescence and corresponding increase in green fluorescence.

Example 26

Figure 3:
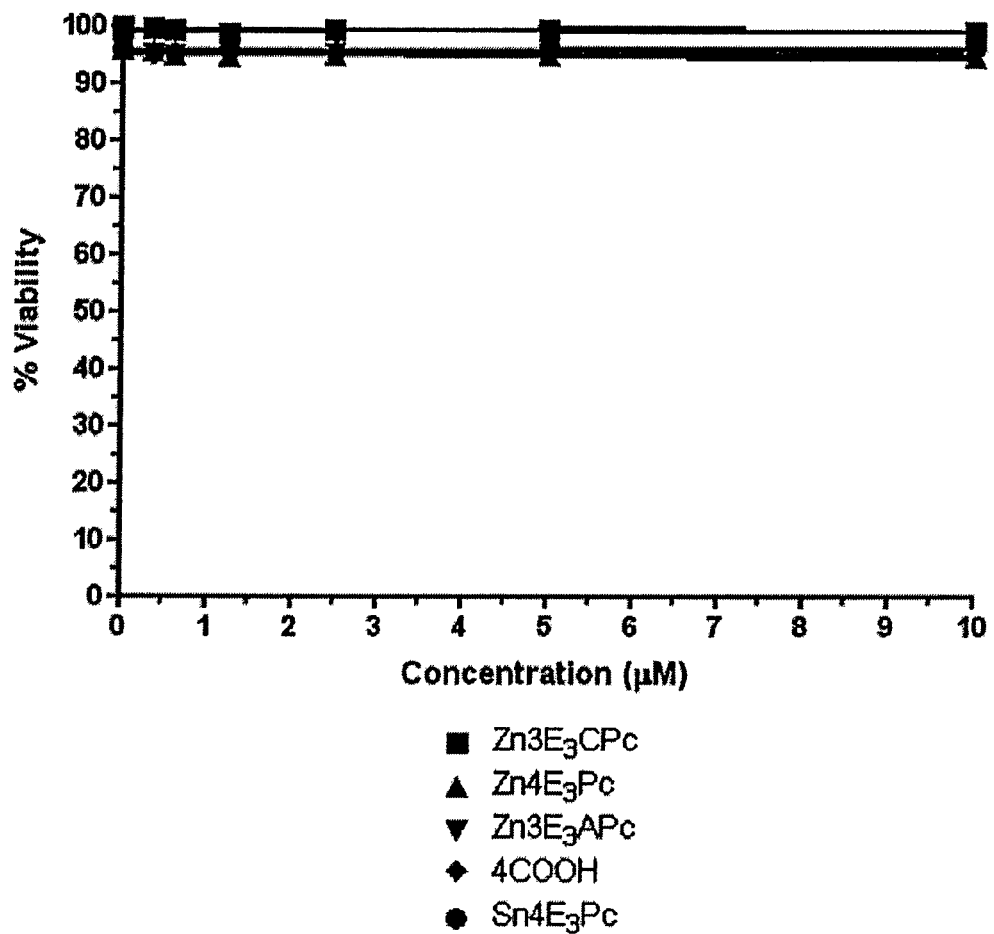
FIG. 3 depicts the change in cell viability as a function of concentration of a series of Pc compounds without radiation (dark cytotoxicity).
Figure 4:
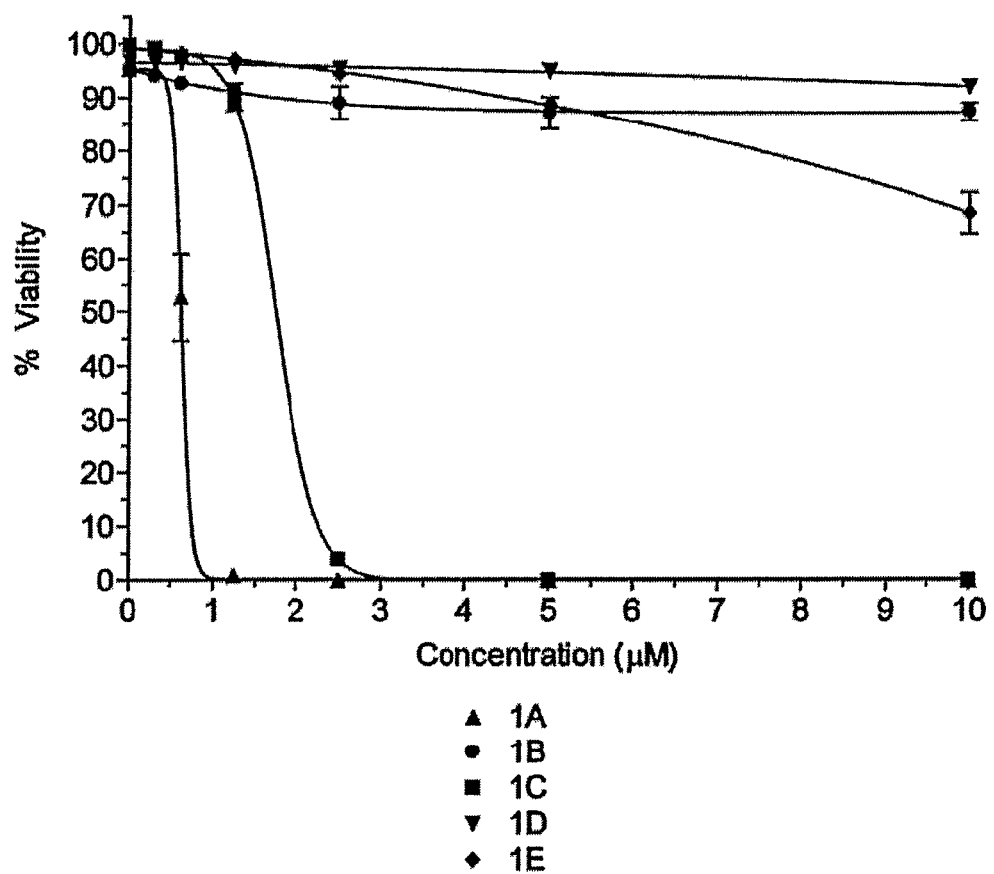
FIG. 4 depicts the change in cell viability as a function of concentration of compounds 1A-1E with near-IR radiation (light cytotoxicity).

Several of the novel Pc compounds were observed to be readily taken up by cells, to have low cytotoxicity in the absence of near-IR light ($IC_{50}$>100 µM), but to be highly toxic when the cells were exposed to light >610 nm ($IC_{50}$<5 µM). FIG. 3 shows that these compounds were stable in the absence of light, while FIG. 4 shows the phototoxicity of 1A and 1C at even relatively low concentrations of the order of 1-3 µM; 1E also showed some phototoxicity. Such high phototoxicity, for example, towards human cancer cells may be used in photodynamic therapy applications. Without wishing to be bound by this theory, it appears that the rapid cell death at such low concentration is caused by the specific deposition of the dye within sensitive cell organelles, such as the mitochondrial nuclei, and endoplasmic reticulum (ER), with an apoptotic mechanism of action. Interestingly, compound 1B, with identical substituents to the compound 1A, was found to be readily taken up by human HEp2 cells, but showed neither dark nor light-induced toxicity, possibly due to preferential localization within cell vesicles and lysosomes.

Example 27

We have developed conditions for the conjugation of ZnPc 1C and 1E to oligonucleotides [e.g., 5'($NH_2(CH_2)_{12}$-GTAAAACGACGGCCAGT-3' or 5'($NH_2(CH_2)_6$-GTAAAACGACGGCCAGT-3']. The conjugates were purified by HPLC, and their absorption and fluorescence properties studied and compared with the unconjugated ZnPcs. We observed only a slight red-shift in the emission maxima of the bioconjugates as compared with the unconjugated dyes. Furthermore, we observed no non-specific binding between the ZnPcs and the oligonucleotide.

Example 28

Succinimide esters were reacted with primary amines for oligonucleotide-phthalocyanine conjugations. The protocol had two principal steps: first, the succinimide ester of the phthalocyanine carboxylic group(s) was obtained by reaction with DCC and NHS in anhydrous conditions, and then it was conjugated to amino-modified oligonucleotide using the following procedure: 200 nM of phthalycianine succimide ester (approximately 14 µL of 10 mM solution in DMSO was mixed with 7 µL of water (carbonate or borate buffer, pH 7.5-8.5), 75 µL of the labeling buffer, and 20 nM of the oligonucleotide (approximately 4 µL of 5 mM solution). The reaction was incubated at room temperature for 15-18 hours. Labeled oligonucleotide was purified by ethanol precipitation and by reverse-phase HPLC ($C_{18}$ column, 0.1M TEAA-MeOH gradient, fluorescent and DAD detection). The isolated fractions were concentrated in a rotary evaporator and dried in high vacuum (<0.01 mm Hg) at room temperature.

Figure 5:
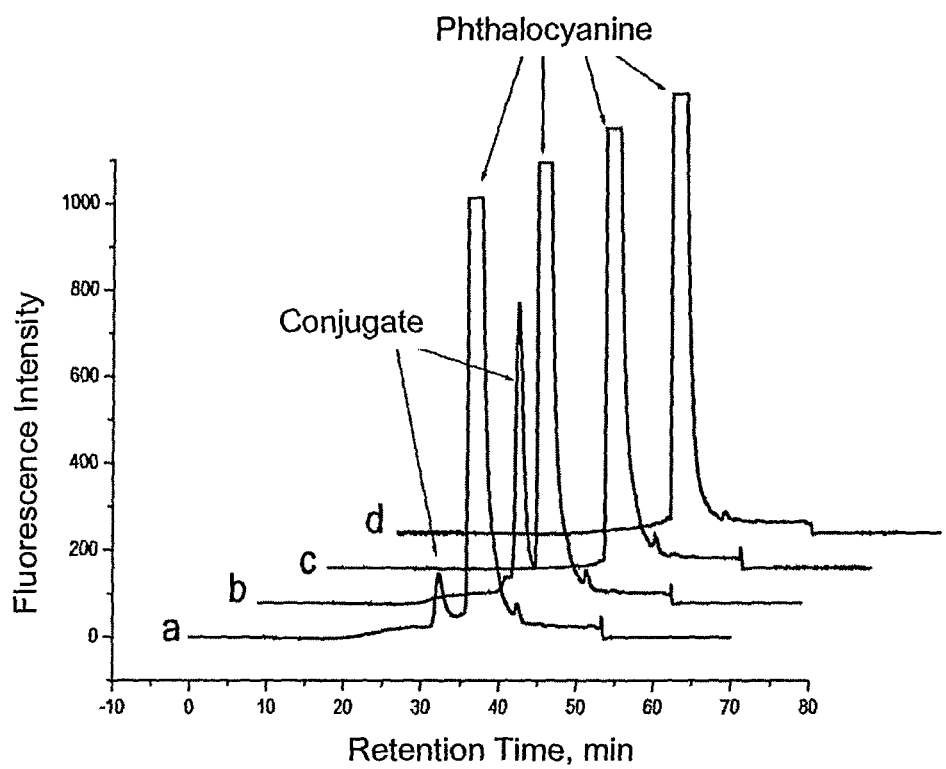
FIG. 5 depicts chromatograms of reaction mixtures and of dye control, showing fluorescence versus retention time.

The resulting conjugates formed via covalent bonding between the amino group of the modified oligonucleotide and the succinimide group of the metallophthalocyanine esters, rather than via non-specific interactions. An experiment involving inactivated dye (i.e., carboxylic acid instead of succinimide ester) and amino-modified oligonucleotide was also conducted. The reaction was prepared and treated with similar conditions as for the succinimide esters, but did not produce any labeled product as monitored by HPLC with DAD and fluorescence detection, as shown in FIG. 5. FIG. 5 displays the chromatograms of the reaction mixtures (a-linker C, b-linker $C_{12}$) and a control reaction with 1E (trace c), which was inactive. This experiment demonstrated the absence of non-covalent binding between the dye and oligonucleotide.

Example 29

The phthalocyanines 1E and 1C were used to label primers for PCR amplifications of different size regions of an M13 mp18 ssDNA template, and a 98 bp region of exon-10 of the CFTR gene (used for detection of dF508 mutation, which is associated with cystic fibrosis), using standard protocols. The PCR primers used are listed in Table 1.

TABLE 1

Sequences of oligonucleotide primers used in the PCR amplifications.

| Oligos | Sequence (5'→3') | $T_m$ (° C.) | Seq ID |
|---|---|---|---|
| M13mp18 primer1[a] | GTA AAA CGA CGG CCA GT | 52.6° C. | SEQ 1 |
| M13mp18 primer2 for 381 bp product | CAA CTC TCT CAG GGC CAG | 55.0° C. | SEQ 2 |
| M13mp18 primer2 for 272 bp product | GGC CGA TTC ATT AAT GCA GC | 54.8° C. | SEQ 3 |
| M13mp18 primer2 for 185 bp product | ACT CTA TAG GCA CCC CGA | 54.2° C. | SEQ 4 |
| M13mp18 primer2 for 135 bp product | GTG TGG AAT TGT GAG CG | 51.3° C. | SEQ 5 |
| CFTR1 primer1[a] | GTT GGC ATG CTT TGA TGA CGC TTC | 59.4° C. | SEQ 6 |
| CFTR1 primer2 | GTT TTC CTG GAT TAT GCC TGG GCA C | 60.3° C. | SEQ 7 |

[a] This primer, modified with an amino-group attached to 5' end, was labeled with either 1C or 1E.

PCR cocktails contained 1 μL of each of the primers (final concentration of approximately 1 μM), 2 μL of dNTP's (final concentration of each, 0.2 mM), 10 μL of PCR buffer, 1 μL of Taq DNA Polymerase (final concentration of 0.5 unit/μL), 1 μL of DNA template (final concentration of 2 ng/μL) and 84 μL of PCR qualified water. PCR was carried out using a commercial thermal cycling machine (Eppendorf or Techne). M13mp18 ssDNA amplification used the following for 30 cycles of: 94° C. for 30 s, 57° C. for 40 s, 72° C. for 60 s; and a final extension at 72° C., followed by a cooling step to 4° C. Thermal cycles for CFTR gene amplification used an initial denaturation step at 94° C. for 5 minutes followed by 30 cycles of: 94° C. for 40 s, 62° C. for 40 s, 72° C. for 60 s; and a final extension at 72° C., followed by a cooling step to 4° C.

Example 30

For the samples described in Example 30, the amplicons were detected by electrophoresis on agarose gel (UV detection after staining with ethidium bromide) as shown in FIGS. 6d and 6e, and on polyacrylamide gel (NIR fluorescence detection at 700 nm), as shown in FIG. 6a-c. Images taken of the gels indicated that the appropriate length products were generated (as indexed against standard DNA size markers) with high fidelity. The PCR products of different sizes (98-381 base pairs) were obtained using primers labeled with 1C (see FIG. 6a) or 1E (see FIGS. 6b and 6c). FIGS. 6a, b, d & e show images of products of M13mp18 amplification, while FIG. 6c shows the image of a CFTR gene amplification. The results showed that the labeled primers were incorporated into DNA via PCR, and then successfully detected using the fluorescence of phthalocyanine moieties (even in 100% aqueous media).

Example 31

Figure 7:
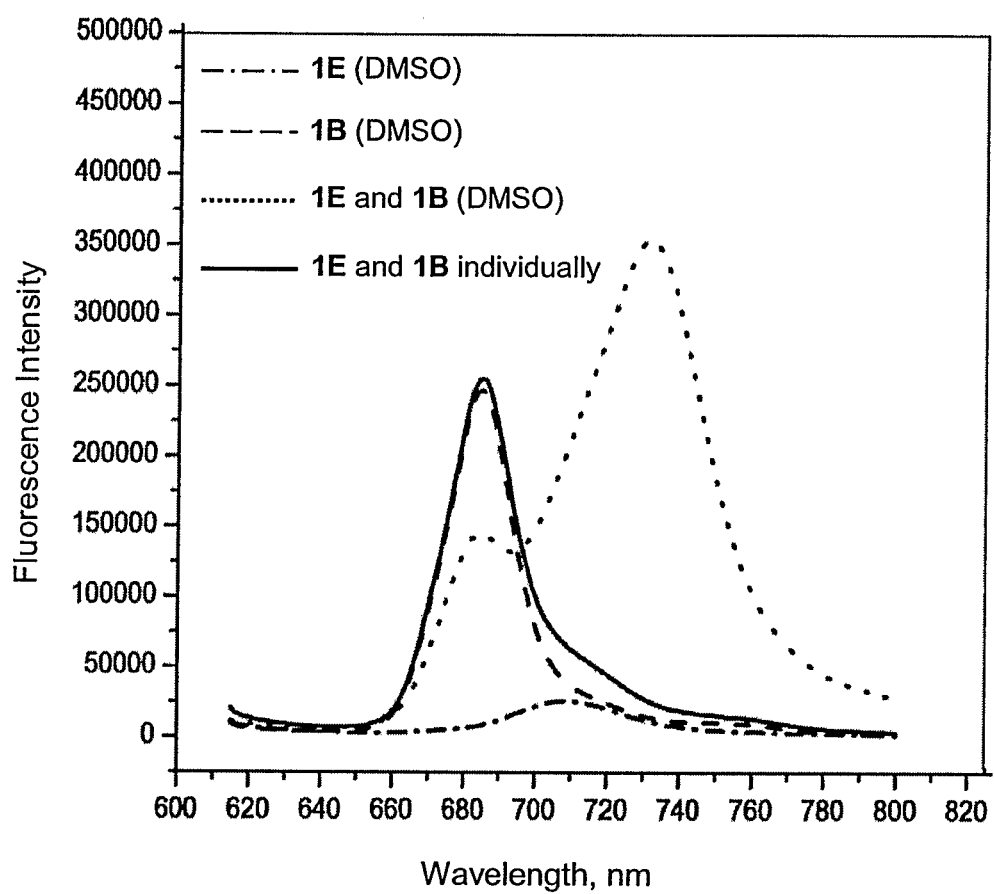
FIG. 7 depicts fluorescence intensity versus wavelength for compounds 1B and 1E, separately and mixed.

Different fluorescence detection methods may be used, including fluorescence resonance energy transfer (FRET), resonance energy transfer (RET), and single molecule detection and spectroscopy. We have observed some unique characteristics associated with the Pc-dyes that make them ideal for a variety of bioanalytical applications requiring fluorescence transduction. As an example, we have been developing new quencher systems for near-IR Pc dyes that can be incorporated into "molecular beacons" to transduce DNA/DNA interactions. FIG. 7 shows the significant enhancement of 1B fluorescence emission in the presence of 1E. This enhancement demonstrated the efficient FRET occurring between the two molecules.

Example 32

Phthalocyanine compounds 1E and 1B were used for ultra-sensitive FRET-based applications in the near-IR. The experiments were performed in DMSO solutions containing 2.2 μM of 1E, 13 μM of 1B and a mixture of those compounds at the same concentrations. An excitation wavelength of 605 nm appeared to cause excitation primarily of 1E. All measurements were performed in "front face" mode to mitigate potential inter-filter effects. The results (FIG. 7) demonstrated significant enhancement of 1B emission in the presence of 1E, which indicated the efficient FRET between the two molecules.

Example 33

Figure 9A:
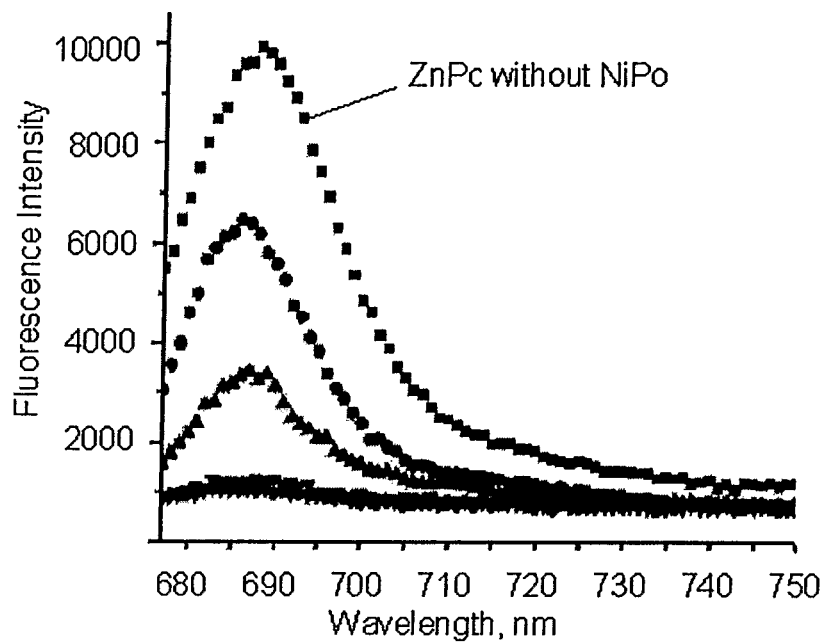
FIG. 9 depicts decreasing fluorescence intensity versus wavelength for Zn-Pc (1E) with increasing concentrations of Ni-Pc (9A), and of ZnPc (1E) with increasing concentrations of BHQ-3 (9B).
Figure 9B:
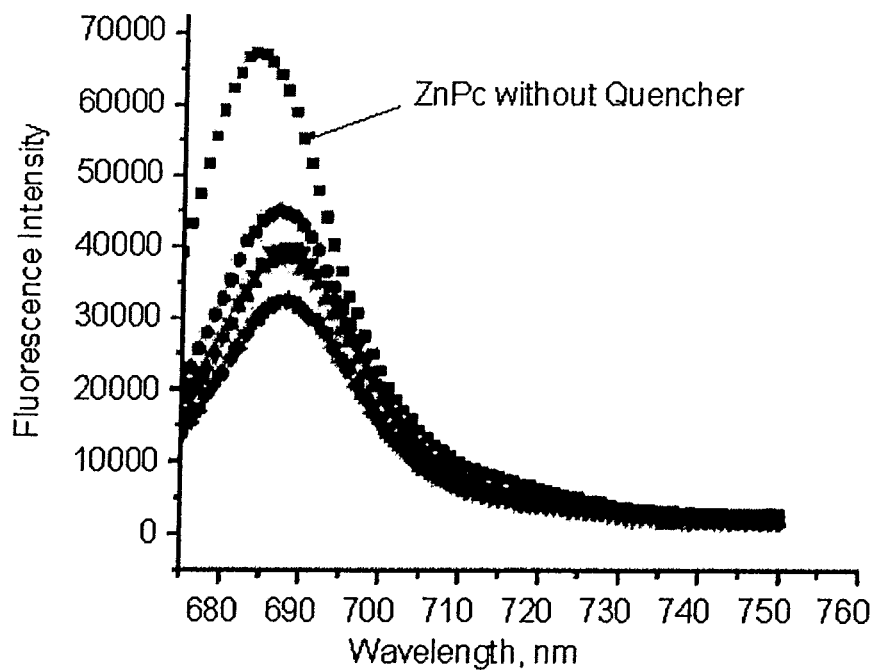

A Zn-Pc was used as a fluorescence reporter, and a Ni-Pc was used as a quencher in a RET assay. The quenching properties of Ni-Pc were compared to a far red quencher (BHQ-3) using a Stern-Volmer analysis. FIG. 9 shows the that the fluorescence intensity decreased with increasing quencher concentration. FIG. 9A shows the results we obtained using NiPc as the quencher, and FIG. 9B shows the results we obtained using a commercial quencher, BHQ-3. The Stern-Volmer quenching constants were determined to be 0.0004 $M^{-1}$ and 0.013 $M^{-1}$ for BHQ-3 and Ni-Pc, respectively, indicating the utility of the non-fluorescent metal Pc as quenchers for far-infrared dyes.

Example 34

The near-IR fluorescence emitted from a metal-Pc dye exhibits both excellent photostability and signal-to-noise ratio. These two characteristics have allowed single molecule-based detection. The photostability for a fluorophore is important for both biodetection and imaging applications. For example, highly photostable fluorophores provide long observation periods when they are used as imaging reagents. In single molecule experiments, high photon yields per molecule combined with high photostability allows one to obtain excellent signal-to-noise ratios. We have demonstrated the advantages of using near-IR fluorescence for single molecule detection experiments, resulting from the significant reduction in background observed when using near-IR excitation. In these experiments, Pc dye (1E) had much better photostability relative to carbocyanine-based dyes such as IRD700 and DOTCI, as shown in FIG. 8.

The complete disclosures of all references cited in this specification are hereby incorporated by reference. In the event of an otherwise irreconcilable conflict, however, the present specification shall control.

What is claimed:

1. A compound having the structure:

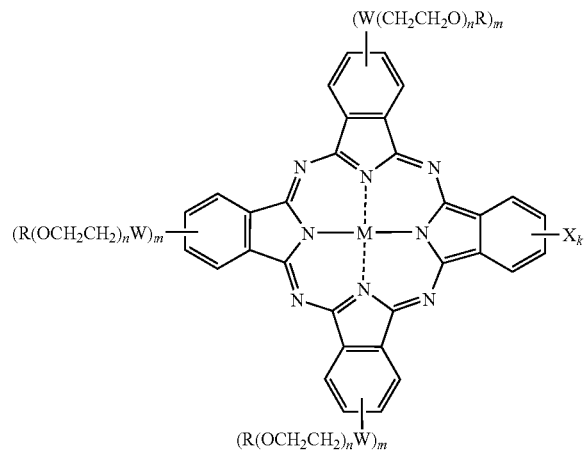

wherein

M is selected from the group consisting of 2H, Zn, Ni, Cu, SnY$_2$, Pd, AlY, Pt, SiY$_2$, GaY, and CoY;

Y is selected from the group consisting of F, Cl, Br, I, OR, OH, SR, —CCR, C=CR, OPh, CH$_3$, C$_2$H$_5$, Pr, i-Pr, Bu, i-Bu, Ph and mixtures thereof;

n is 3, 4, 5, or 6; wherein each n is the same;

m is 1 or 2; wherein the m's may be the same or different;

k is 1 or 2;

R is selected from the group consisting of CH$_3$, H, CH$_2$CH$_3$, iPr, iBu, and SO$_3$H, wherein the R's may be the same or different;

W is selected from the group consisting of O, S, and NH, wherein each W is the same;

X is selected from the group consisting of —O-Ph-CO$_2$H, NH$_2$, NO$_2$, SO$_3$H, O(CH$_2$CH$_2$)$_n$OR', —N=C=S, —NH(CO)CH$_2$Cl, —NH(CO)CH$_2$Br, —NH(CO)CH$_2$I, —NH(CO)NHNH$_2$, —OPh-(CO)H, —O-Ph-(CO)NHNH$_2$; —NHCO(CH$_2$)$_j$COOH;

j is from 2 to 12;

R' is selected from the group consisting of CH$_3$, H, CH$_2$CH$_3$, iPr, iBu, and SO$_3$H; and X and R(OCH$_2$CH$_2$)$_n$W are different.

2. A compound as recited in claim 1, wherein each m is 1 and k is 1.

3. A compound as recited in claim 1, wherein each m is 1, k is 1, M is Zn, n is 3, W is O, each R is CH$_3$, and X is

4. A compound as recited in claim 1, wherein each m is 1, k is 1, M is Zn, n is 3, W is O, each R is CH$_3$, and X is —NH$_2$.

5. A compound as recited in claim 1, wherein said compound has the structure:

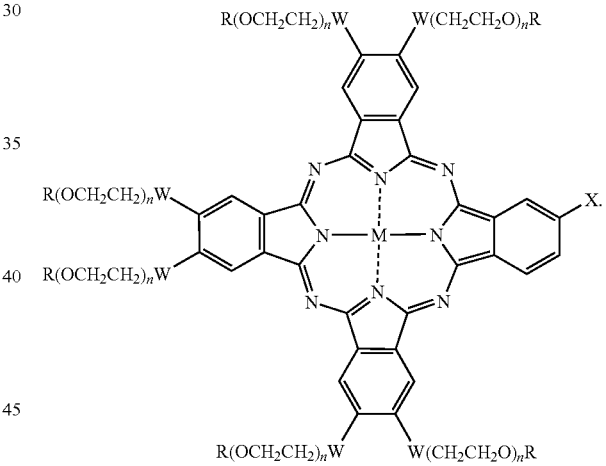

6. A compound as recited in claim 1; wherein said compound has the structure:

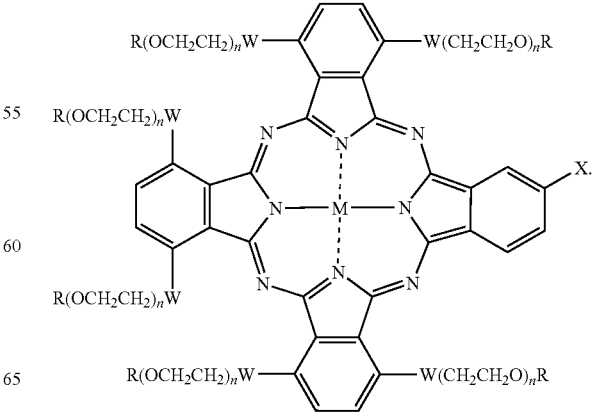

7. A compound as recited in claim 1; wherein said compound has the structure:

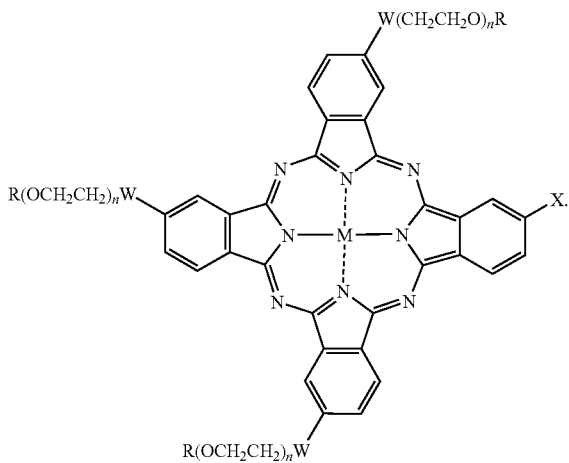

8. A compound having the structure:

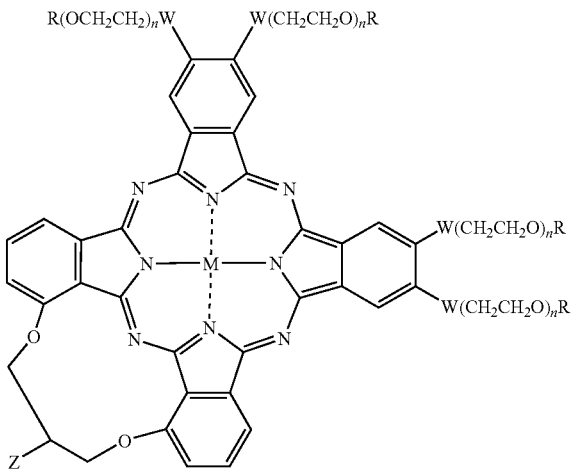

wherein:
M is selected from the group consisting of 2H, Zn, Ni, Cu, SnY$_2$, Pd, AlY, Pt, SiY$_2$, GaY, and CoY;
Y is selected from the group consisting of F, Cl, Br, I, OR, OH, SR, —CCR, C=CR, OPh, CH$_3$, C$_2$H$_5$, Pr, i-Pr, Bu, i=Bu, Ph and mixtures thereof;
n is 3, 4, 5, or 6; wherein each n is the same;
R is selected from the group consisting of CH$_3$, H, CH$_2$CH$_3$, iPr, iBu, and SO$_3$H; wherein the R's may be the same or different;
W is selected from the group consisting of O, S, and NH; wherein each W is the same;
Z is selected from the group consisting of NR"R'", SR" and OR", where R" and R'" are selected from the group H, Ph-CO$_2$H, O, ((CH$_2$)$_n$)$_m$OR, C=S, (CO)CH$_2$Br, (CO)CH$_2$I, (CO)NHNH$_2$, Ph(CO)H, Ph(CO)NHNH$_2$, and $_{CO}$(CH$_2$)COOH, wherein R" and R'" may be different or the same.

9. A compound as recited in claim 1; wherein said compound has the structure:

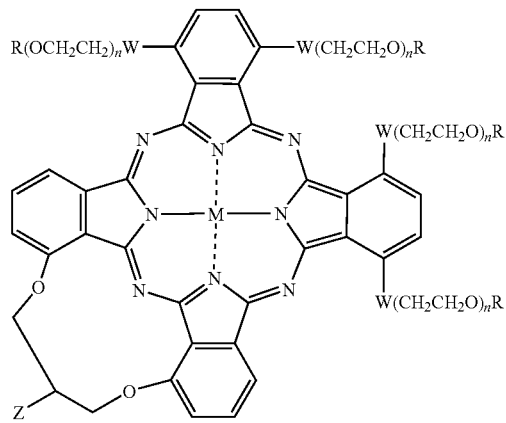

wherein:
M is selected from the group consisting of 2H, Zn, Ni, Cu, SnY$_2$, Pd, AlY, Pt, SiY$_2$, GaY, and CoY;
Y is selected from the group consisting of F, Cl, Br, I, OR, OH, SR, —CCR, C=CR, OPh, CH$_3$, C$_2$H$_5$, Pr, i-Pr, Bu, i=Bu, Ph and mixtures thereof;
n is 3, 4, 5, or 6; wherein each n is the same;
R is selected from the group consisting of CH$_3$, H, CH$_2$CH$_3$, iPr, iBu, and SO$_3$H; wherein the R's may be the same or different;
W is selected from the group consisting of O, S, and NH; wherein each W is the same;
Z is selected from the group consisting of NR"R'", SR" and OR", where R" and R'" are selected from the group H, Ph-CO$_2$H, O, ((CH$_2$)$_n$)$_m$OR, C=S, (CO)CH$_2$Br, (CO)CH$_2$I, (CO)NHNH$_2$, Ph(CO)H, Ph(CO)NHNH$_2$, and CO(CH$_2$)COOH, wherein R" and R'" may be different or the same.

10. A compound having the structure:

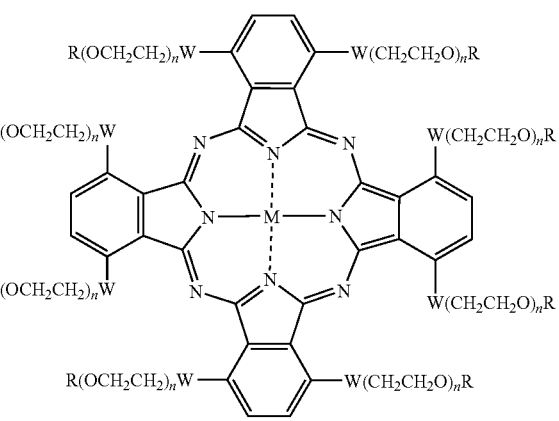

wherein
M is selected from the group consisting of 2H, Zn, Ni, Cu, SnY$_2$, Pd, AlY, Pt, SiY$_2$, GaY, and CoY;
Y is selected from the group consisting of F, Cl, Br, I, OR, OH, SR, —CCR, C=CR, OPh, CH$_3$, C$_2$H$_5$, Pr, i-Pr, Bu, i=Bu, Ph and mixtures thereof;
n is 3, 4, 5, or 6; wherein each n is the same;
R is selected from the group consisting of CH$_3$, H, CH$_2$CH$_3$, iPr, iBu, and SO$_3$H; where the R's may be the same or different; and W is selected from the group consisting of O, S, and NH; wherein each W is the same.

11. A method for staining mitochondria in living cells; said method comprising the steps of:
   (a) contacting the cells with a compound as recited in claim 1, wherein the compound is taken up by the cells and preferentially binds to mitochondria; and
   (b) observing the distribution of said compound by near-infrared fluorescence.

12. A method for staining endoplasmic reticulum in living cells; said method comprising the steps of:
   (a) contacting the cells with a compound as recited in claim 1, wherein the compound is taken up by the cells and preferentially binds to endoplasmic reticulum; and
   (b) observing the distribution of said compound by near-infrared fluorescence.

13. A method for inducing apoptosis in living cells; said method comprising the steps of:
   (a) contacting the cells with a compound as recited in claim 1, wherein said compound is taken up by the cells; and
   (b) exposing the cells to sufficient near-infrared irradiation to induce apoptosis in the irradiated cells that have taken up the compound; wherein said apoptosis occurs at a rate that is substantially greater than the rate of apoptosis in otherwise similarly situated cells that have taken up the compound but that have not been exposed to near-infrared radiation; and at a rate that is substantially greater than the rate of apoptosis in otherwise similarly situated cells that have not taken up said compound and that have been exposed to near-infrared radiation.

14. A method for assaying the proximity of a first moiety and a second moiety within a living cell, wherein the two moieties are two different molecules, or are different parts of a single molecule; wherein the first moiety is covalently bound to a fluorophore; wherein the second moiety is covalently bound to a fluorescence quencher; wherein the fluorescence of the fluorophore is repressed by proximity to the quencher as a function of the distance between the fluorophore and the quencher; said method comprising contacting the cell with the first and second moieties and then observing the intensity of fluorescence from the fluorophore; wherein the fluorophore and quencher are both compounds as recited in claim 1; and wherein the fluorophore and the quencher may be the same or different.

15. A method for staining endosomes in living cells; said method comprising the steps of:
   (a) contacting the cells with a compound as recited in claim 1, wherein the compound is taken up by the cells and preferentially binds to endosomes; and
   (b) observing the distribution of the compound by near-infrared fluorescence.

16. A method for assaying the proximity of a first moiety and a second moiety within a living cell, wherein the two moieties are two different molecules, or are different parts of a single molecule; wherein the first moiety is covalently bound to a fluorophore; wherein the second moiety is covalently bound to a chromophore; wherein the fluorescence of the fluorophore is enhanced by proximity to the chromophore as a function of the distance between the fluorophore and the chromophore; said method comprising contacting the cell with the first and second moieties and then observing the intensity of fluorescence from the fluorophore; wherein the fluorophore and chromophore are both compounds as recited in claim 1; and wherein the fluorophore and the chromophore may be the same or different.

17. A method for labeling a biomolecule and detecting the labeled biomolecule in a sample; said method comprising conjugating the biomolecule with a compound as recited in claim 1, introducing the labeled biomolecule into the sample, and observing the distribution of the labeled biomolecule by near-infrared fluorescence.

18. A method as recited in claim 17, wherein said method is used to differentially label oligonucleotide products produced by a polymerase chain reaction amplification, wherein the labels used for the different bases may be distinguished from one another by different fluorescence absorption, different fluorescence emission, or different fluorescence lifetimes, but without having substantially different electrophoretic mobilities among the different labels used.

* * * * *